(12) United States Patent
McShane, III et al.

(10) Patent No.: US 10,478,312 B2
(45) Date of Patent: Nov. 19, 2019

(54) IMPLANT WITH PROTECTED FUSION ZONES

(71) Applicant: Institute for Musculoskeletal Science and Education, Ltd., Wayne, PA (US)

(72) Inventors: Edward J. McShane, III, Collegeville, PA (US); Christopher J. Ryan, Lincoln University, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 362 days.

(21) Appl. No.: 15/334,022

(22) Filed: Oct. 25, 2016

(65) Prior Publication Data

US 2018/0110626 A1 Apr. 26, 2018

(51) Int. Cl.
*A61F 2/44* (2006.01)
*A61F 2/46* (2006.01)
*A61F 2/30* (2006.01)

(52) U.S. Cl.
CPC ............ *A61F 2/446* (2013.01); *A61F 2/4455* (2013.01); *A61F 2/4611* (2013.01); *A61F 2002/30029* (2013.01); *A61F 2002/3093* (2013.01); *A61F 2002/30136* (2013.01); *A61F 2002/30172* (2013.01); *A61F 2002/30289* (2013.01); *A61F 2002/30322* (2013.01); *A61F 2002/4495* (2013.01)

(58) Field of Classification Search
CPC .. A61F 2/446; A61F 2002/443; A61F 2/4622; A61F 2002/30029; A61F 2002/30289; A61F 2002/30322; A61F 2/447; A61F 2002/4495; A61F 2/4455
See application file for complete search history.

(56) References Cited

U.S. PATENT DOCUMENTS

| 3,867,728 A | * | 2/1975 | Stubstad ............. A61F 2/30907 128/DIG. 21 |
| 4,961,740 A | | 10/1990 | Ray et al. |
| 5,458,638 A | | 10/1995 | Kuslich et al. |

(Continued)

FOREIGN PATENT DOCUMENTS

| WO | 2009-051779 A1 | 4/2009 |
| WO | 2009051779 A1 | 4/2009 |

(Continued)

OTHER PUBLICATIONS

International Search Report and Written Opinion for PCT application PCT/US2016/029865 dated Aug. 19, 2016.

(Continued)

*Primary Examiner* — Matthew J Lawson
(74) *Attorney, Agent, or Firm* — Plumsea Law Group, LLC

(57) ABSTRACT

An implant for use in a spine includes a body and a plurality of structural members. The plurality of structural members includes outer members that are arranged to contact a vertebra upon implantation and support members that provide reinforcement and stability to the outer members. The outer members may have sections with a generalized helical geometry. The generalized helical geometry provides distal and proximal outwardly facing surface regions and creates a series of protected fusion zones along the superior and inferior surfaces of the implant to foster adjacent bone growth.

21 Claims, 23 Drawing Sheets

(56) References Cited

U.S. PATENT DOCUMENTS

| | | |
|---|---|---|
| 5,571,192 A | 11/1996 | Schonhoffer |
| 5,607,424 A | 3/1997 | Tropiano |
| 5,609,635 A | 3/1997 | Michelson |
| 5,658,337 A | 8/1997 | Kohrs et al. |
| 5,709,683 A | 1/1998 | Bagby |
| 5,716,416 A | 2/1998 | Lin |
| 5,897,556 A | 4/1999 | Drewry et al. |
| 6,039,762 A | 3/2000 | McKay |
| 6,090,143 A | 7/2000 | Meriwether et al. |
| 6,126,689 A | 10/2000 | Brett |
| 6,149,651 A | 11/2000 | Drewry et al. |
| 6,200,348 B1 | 3/2001 | Biedermann et al. |
| 6,206,924 B1 | 3/2001 | Timm |
| 6,371,987 B1 | 4/2002 | Weiland et al. |
| 6,428,575 B2 | 8/2002 | Koo et al. |
| 6,436,141 B2 | 8/2002 | Castro et al. |
| 6,447,543 B1 * | 9/2002 | Studer .................. A61F 2/2846 623/17.11 |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,537,320 B1 | 3/2003 | Michelson |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,141,068 B2 | 11/2006 | Ross et al. |
| 7,186,267 B2 | 3/2007 | Aston et al. |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,485,134 B2 | 2/2009 | Simonson |
| 7,527,649 B1 | 5/2009 | Blain |
| 7,537,616 B1 | 5/2009 | Branch et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,794,500 B2 | 9/2010 | Felix |
| 7,799,056 B2 | 9/2010 | Sankaran |
| 7,803,191 B2 | 9/2010 | Biedermann et al. |
| 7,879,103 B2 | 2/2011 | Gertzman |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,298,286 B2 | 10/2012 | Trieu |
| 8,328,848 B2 | 12/2012 | Lowery et al. |
| 8,361,149 B2 | 1/2013 | Castro |
| 8,414,820 B2 | 4/2013 | Bertele et al. |
| 8,430,930 B2 | 4/2013 | Hunt |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,613,769 B2 | 12/2013 | Sears et al. |
| 8,623,090 B2 * | 1/2014 | Butler .................. A61F 2/442 623/17.15 |
| 8,673,006 B2 | 3/2014 | Castro |
| 8,709,042 B2 | 4/2014 | Greenhalgh et al. |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,932,356 B2 | 1/2015 | Kraus |
| 8,940,052 B2 | 1/2015 | Lechmann et al. |
| 8,951,300 B2 | 2/2015 | Parrish |
| 8,986,383 B2 | 3/2015 | Castro |
| 9,039,766 B1 | 5/2015 | Fonte |
| 9,173,746 B2 | 11/2015 | Lowery et al. |
| 9,186,252 B2 | 11/2015 | Leibinger |
| 9,186,257 B2 | 11/2015 | Geisler et al. |
| 9,247,970 B2 | 2/2016 | Teisen |
| 9,271,845 B2 | 3/2016 | Hunt et al. |
| 9,295,562 B2 | 3/2016 | Lechmann et al. |
| 9,402,733 B1 | 8/2016 | To et al. |
| 9,408,651 B2 | 8/2016 | Sennett et al. |
| 9,421,108 B2 | 8/2016 | Hunt |
| 9,814,578 B1 * | 11/2017 | Gotfried ............ A61B 17/8095 |
| 2001/0014826 A1 | 8/2001 | Biedermann et al. |
| 2001/0032012 A1 | 10/2001 | Castro et al. |
| 2002/0052656 A1 | 5/2002 | Michelson |
| 2003/0078660 A1 | 4/2003 | Clifford et al. |
| 2003/0083746 A1 | 5/2003 | Kuslich |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0027364 A1 * | 2/2005 | Kim .................. A61F 2/4425 623/17.13 |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2006/0041262 A1 | 2/2006 | Calvert et al. |
| 2006/0052872 A1 * | 3/2006 | Studer .................. A61F 2/4425 623/17.13 |
| 2006/0100706 A1 | 5/2006 | Shadduck et al. |
| 2006/0147332 A1 | 7/2006 | Jones et al. |
| 2006/0293753 A1 | 12/2006 | Thramann |
| 2007/0027544 A1 | 2/2007 | McCord et al. |
| 2007/0050032 A1 | 3/2007 | Gittings et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0077244 A1 | 3/2008 | Robinson |
| 2008/0306595 A1 | 12/2008 | McLeod et al. |
| 2008/0312742 A1 | 12/2008 | Abernathie |
| 2009/0036985 A1 | 2/2009 | Whiting |
| 2009/0048678 A1 | 2/2009 | Saal et al. |
| 2009/0112321 A1 | 4/2009 | Kitchen |
| 2009/0149958 A1 | 6/2009 | Prewett et al. |
| 2009/0248162 A1 | 10/2009 | Peckham |
| 2010/0286778 A1 | 11/2010 | Eisermann et al. |
| 2010/0286783 A1 * | 11/2010 | Lechmann ............ A61F 2/3094 623/17.12 |
| 2011/0015741 A1 | 1/2011 | Melkent et al. |
| 2011/0066192 A1 | 3/2011 | Frasier et al. |
| 2011/0166660 A1 | 7/2011 | Laurence |
| 2011/0172775 A1 * | 7/2011 | Flickinger ............ A61F 2/4465 623/17.16 |
| 2011/0190895 A1 | 8/2011 | Segal et al. |
| 2011/0245926 A1 | 10/2011 | Kitchen |
| 2011/0270401 A1 | 11/2011 | McKay |
| 2011/0301709 A1 | 12/2011 | Kraus et al. |
| 2011/0313532 A1 * | 12/2011 | Hunt .................... A61F 2/30767 623/18.11 |
| 2012/0191188 A1 | 7/2012 | Huang |
| 2012/0191189 A1 | 7/2012 | Huang |
| 2012/0296431 A1 | 11/2012 | Kim et al. |
| 2013/0030529 A1 | 1/2013 | Hunt |
| 2013/0116793 A1 | 5/2013 | Kloss |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0218282 A1 | 8/2013 | Hunt |

(56) References Cited

U.S. PATENT DOCUMENTS

| | | |
|---|---|---|
| 2013/0218288 A1 | 8/2013 | Fonte et al. |
| 2013/0304211 A1 | 11/2013 | Trautwein et al. |
| 2013/0345812 A1 | 12/2013 | Errico et al. |
| 2014/0058513 A1 | 2/2014 | Gahman et al. |
| 2014/0107785 A1* | 4/2014 | Geisler .................. A61F 2/422 623/17.16 |
| 2014/0121776 A1 | 5/2014 | Hunt |
| 2014/0142707 A1 | 5/2014 | Compton et al. |
| 2014/0195005 A1 | 7/2014 | McKay |
| 2014/0243980 A1 | 8/2014 | Sack et al. |
| 2014/0277457 A1 | 9/2014 | Yeung et al. |
| 2014/0277464 A1 | 9/2014 | Richter et al. |
| 2014/0277569 A1 | 9/2014 | Lange |
| 2014/0288649 A1 | 9/2014 | Hunt |
| 2014/0288650 A1 | 9/2014 | Hunt |
| 2014/0303745 A1 | 10/2014 | Anderson et al. |
| 2014/0309743 A1 | 10/2014 | Falahee |
| 2014/0358246 A1 | 12/2014 | Levy et al. |
| 2015/0127106 A1 | 5/2015 | Partee et al. |
| 2015/0282933 A1 | 10/2015 | Hunt |
| 2015/0282945 A1 | 10/2015 | Hunt |
| 2015/0282946 A1* | 10/2015 | Hunt ........................ A61F 2/28 623/17.16 |
| 2016/0045230 A1 | 2/2016 | Lowery et al. |
| 2016/0081809 A1 | 3/2016 | Schneider et al. |
| 2016/0193057 A1 | 7/2016 | Rhoda |
| 2016/0206439 A1 | 7/2016 | To et al. |
| 2016/0206440 A1 | 7/2016 | DeRidder et al. |
| 2016/0324656 A1* | 11/2016 | Morris ................ A61F 2/30744 |
| 2017/0042697 A1* | 2/2017 | McShane, III ...... A61F 2/30744 |
| 2017/0156878 A1* | 6/2017 | Tsai ........................ A61F 2/442 |
| 2017/0156879 A1* | 6/2017 | Janowski ................ A61F 2/447 |
| 2017/0156880 A1* | 6/2017 | Halverson ............. A61F 2/0077 |
| 2017/0182222 A1* | 6/2017 | Paddock ................... A61F 2/44 |
| 2017/0258606 A1 | 9/2017 | Afzal |
| 2017/0354513 A1* | 12/2017 | Maglaras .............. A61F 2/4455 |

FOREIGN PATENT DOCUMENTS

| | | |
|---|---|---|
| WO | 2010-097632 A1 | 9/2010 |
| WO | 2011-159587 A1 | 12/2011 |
| WO | 2013-019543 A2 | 2/2013 |

OTHER PUBLICATIONS

International Search Report and Written Opinion dated Feb. 5, 2018 for International Application No. PCT/US2017/58006.

* cited by examiner

IMPLANT WITH PROTECTED FUSION ZONES

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, an implant includes a body with a first portion and a second portion, and a structural member with a first end and a second end, where the first end of the structural member is attached to the first portion of the body and the second end of the structural member is attached to the second portion of the body. The structural member has a central member curve. The structural member is exposed on an outer surface of the implant. The central member curve includes a winding segment, and the winding segment of the central member curve winds around a fixed path.

In another aspect, an implant includes a body with a base portion and a keel portion. The keel portion extends in a perpendicular manner from the base portion. The implant also includes an outer member with an elongate geometry, where the outer member includes a first outer member end and a second outer member end. The implant also includes a support member with an elongate geometry, where the support member includes a first support member end and a second support member end. The first outer member end is attached to the base portion and the second outer member end is attached to the keel portion. The first support member end is attached to the base portion and the second support member end is attached to the base portion. The support member is attached to the outer member.

In another aspect, an implant includes a body, where the body includes a transverse plane dividing the implant into a superior half and an inferior half. The implant also includes a first outer member attached to the body, where the first outer member has an elongate geometry. The implant also includes a second outer member attached to the body, where the second outer member has an elongate geometry. The implant also includes a support member attached to the body, where the support member has an elongate geometry. The support member is attached to the first outer member at a first attachment region and the support member is attached to the second outer member at a second attachment region. At the first attachment region the support member is disposed closer to the transverse plane than the first outer member is to the transverse plane; and at the second attachment region the support member is disposed closer to the transverse plane than the second outer member is to the transverse plane.

In another aspect, an implant includes a body and an outer member attached to the body, the outer member having an elongate geometry. The implant also includes a support member with an elongate geometry, where the support member is attached to the body. The outer member having an outwardly facing surface portion, where the outwardly facing surface portion is a curved surface portion including a first distal surface region, a proximal surface region and a second distal surface region. The first distal surface region is configured as a vertebral contacting surface and the second distal surface region is configured as a vertebral contacting surface. The support member is attached to the structural member at a location proximate the proximal surface region.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. The embodiments include implants with a body and one or more structural members. In addition to the various provisions discussed below, any embodiments may make use of any of the body/support structures, frames, plates, coils or other structures disclosed in Morris et al., U.S. Pat. No. 9,918,849, issued on Mar. 20, 2018, and titled "Coiled Implants and Systems and Methods of Use Thereof," which is hereby incorporated by reference in its entirety. For purposes of convenience, the Morris application will be referred to throughout the application as "The Coiled Implant Application". Also, any embodiments may make use of any of the body/support structures, frames, plates or other structures disclosed in McShane III et al., U.S. Publication Number 2019/0000642, published on Jan. 3, 2019, and titled "Implant with Arched Bone Contacting Elements," which is hereby incorporated by reference in its entirety.

Introduction to the Implant

Figure 1:
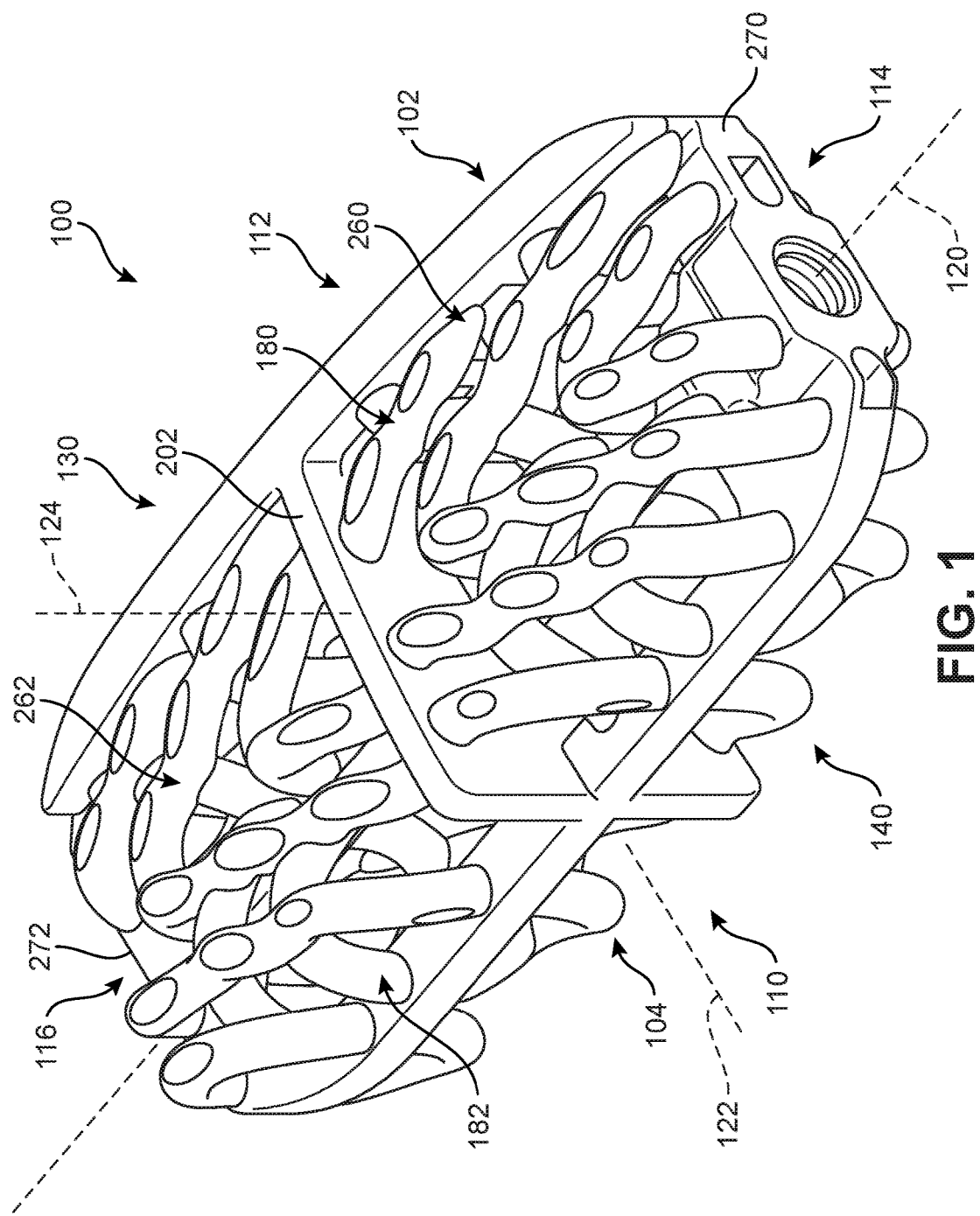
FIG. 1 is an isometric view of a superior side of an implant, according to an embodiment.
Figure 2:
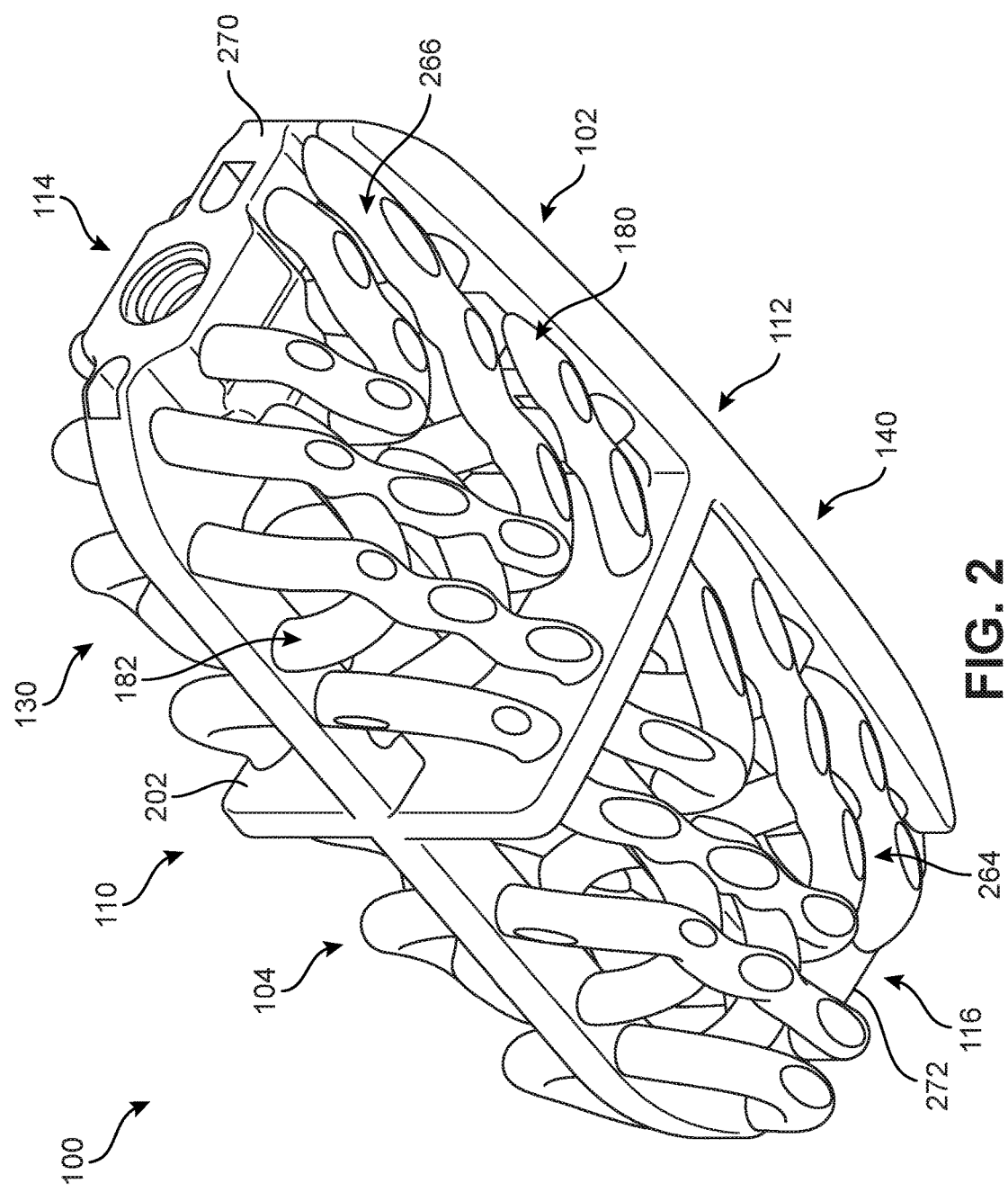
FIG. 2 is an isometric view of an inferior side of an implant, according to an embodiment.

FIGS. 1 and 2 illustrate isometric views of an embodiment of implant 100. Specifically, FIG. 1 is an isometric view of a top or superior side of implant 100, while FIG. 2 is an isometric view of a bottom or inferior side of implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, that is inserted between adjacent vertebrae to provide support and/or facilitate fusion between the vertebrae.

In some embodiments, implant 100 may include a body 102. Body 102 may generally provide a frame or skeleton for implant 100. In some embodiments, implant 100 may also include a plurality of structural members 104. Plurality of structural members 104 may be attached, and/or continuously formed (or "integrally formed") with, body 102.

As used herein, each structural member comprises a distinctive member or element that spans a portion of an implant. Structural members may overlap or intersect, similar to elements in a lattice or other 3D mesh structure. Some embodiments may use structural members in which the length of the member is greater than its width and its thickness. In embodiments where a structural member has an approximately circular cross-sectional shape, the structural member has a length greater than its diameter. In the embodiments seen in FIGS. 1-2, each structural member is seen to have an approximately rounded or circular cross-sectional shape (i.e., the member has the geometry of a solid tube). However, in other embodiments, a structural member could have any other cross-sectional shape, including, but not limited to various polygonal cross-sectional shapes, as well as any other regular and/or irregular cross-sectional shapes. In some cases, for example, the cross-sectional shape of a structural member could vary along its length (e.g., the diameter could change along its length).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides, or portions, facing along a lateral direction of the body (which correspond with the left or right sides of a patient).

In FIGS. 1-2, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Body

Figure 3:
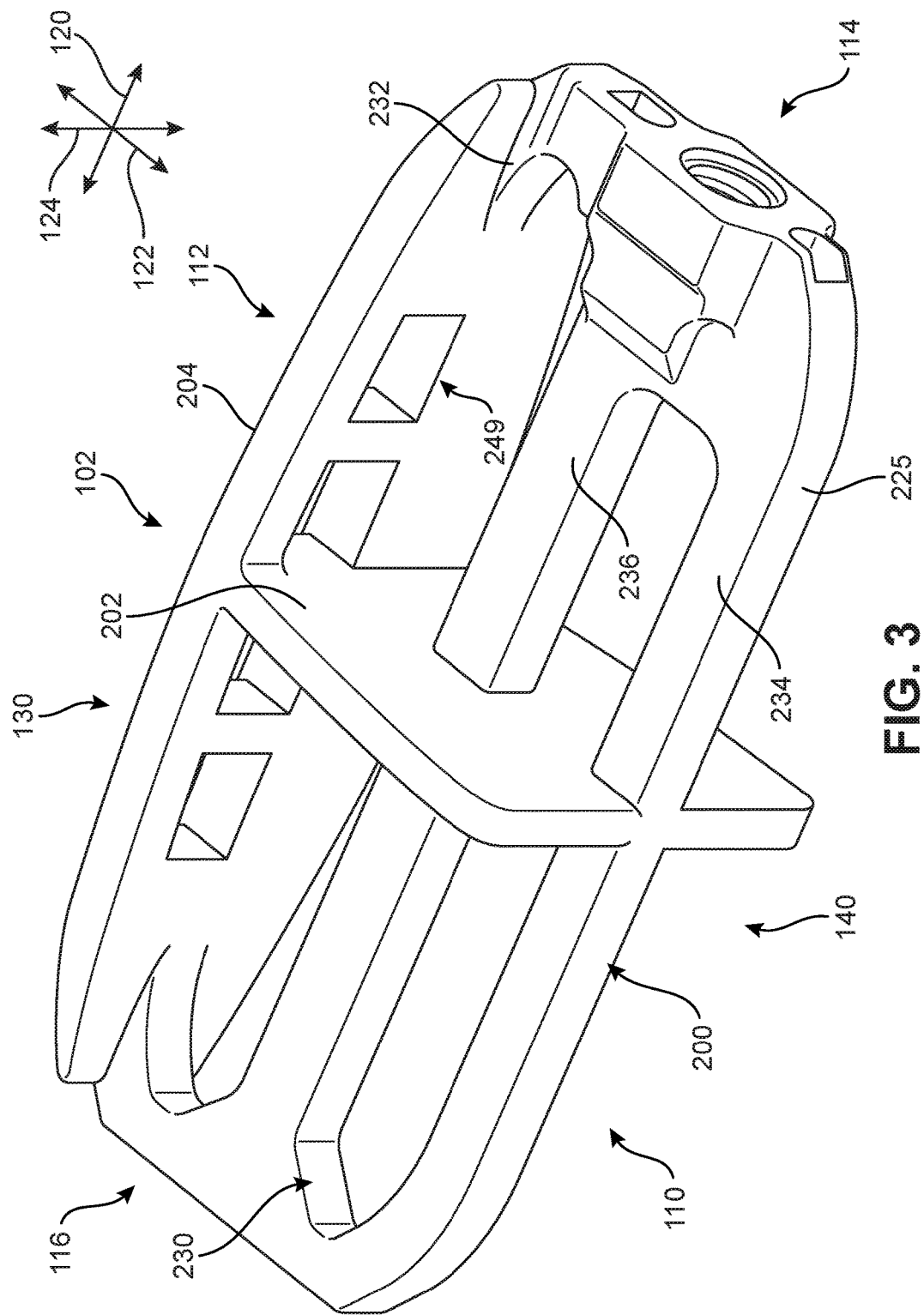
FIG. 3 is an isometric view of a superior side of a body of the implant of FIG. 1 shown in isolation.
Figure 4:
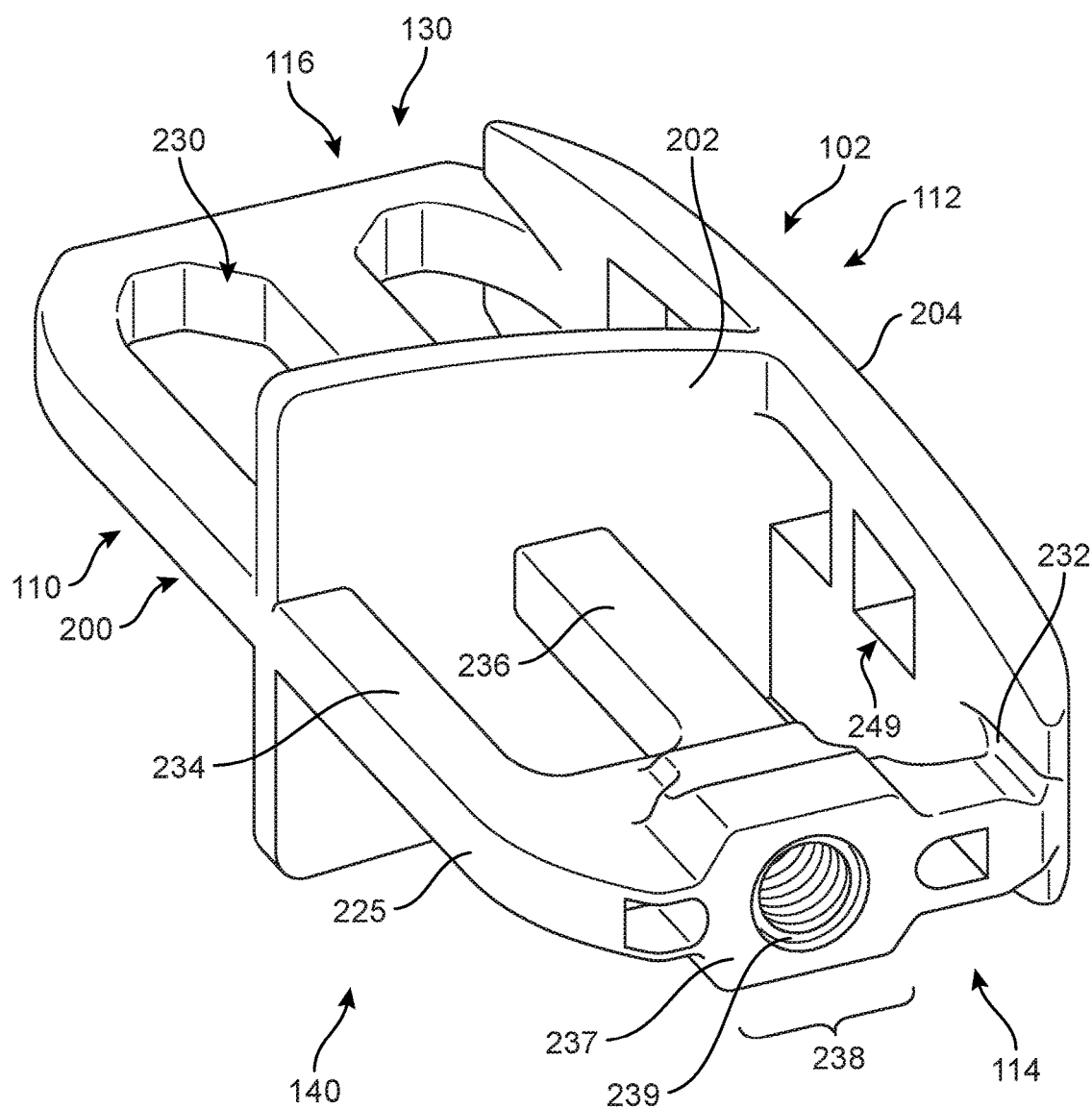
FIG. 4 is a front isometric view of the superior side of the body of FIG. 3.

FIGS. 3 and 4 illustrate schematic isometric views of body 102 in isolation, with plurality of structural members 104 removed for purposes of clarity. In some embodiments, a body could include distinct frame portions that are oriented in different directions. In the embodiment shown in FIGS. 3-4, body 102 includes a base frame portion 200, also referred to as simply "base portion 200". In some embodiments, base portion 200 has a longest dimension aligned with longitudinal axis 120 and a widthwise dimension (e.g., the second longest dimension) aligned with posterior-anterior axis 122 of implant 100. Moreover, in some embodiments, base portion 200 may be characterized as relatively flat and parallel with the transverse plane of implant 100. In some embodiments, base portion 200 may be located approximately half-way between superior side 130 and inferior side 140 (e.g., centrally within implant 100 with respect to vertical axis 124) and may therefore coincide with the transverse plane of implant 100. In other embodiments, however, base portion 200 could be disposed closer to superior side 130 than to inferior side 140 or vice versa.

In the embodiment shown in FIGS. 3-4, body 102 also includes a vertically oriented frame portion, referred to here as central keel portion 202. In some embodiments, central keel portion 202 may have its longest direction oriented along posterior-anterior axis 122 and its width, or second largest dimension, oriented along vertical axis 124. Moreover, in some cases, central keel portion 202 may be located approximately half-way between first lateral side 114 and second lateral side 116 (e.g., centrally within implant 100 with respect to longitudinal axis 120) and may therefore coincide with the median plane of implant 100. In other embodiments, however, central keel portion 202 could be disposed closer to first lateral side 114 than to second lateral side 116 or vice versa.

In some embodiments, one or more sides of an implant (including lateral sides and/or anterior/posterior sides) could include a peripheral frame portion. In the embodiment of FIGS. 3-4, body 102 is seen to include a peripheral frame portion 204 disposed at posterior side 112, which may also be referred to as a "posterior wall" of implant 100. Peripheral frame portion 204 is seen to extend vertically from base portion 200). In contrast, anterior side 110 lacks any frame portion or wall that extends vertically beyond the thickness of base portion 200 in the embodiments of FIGS. 3-4. The presence of frame portion 204 may improve support and strength against vertical loads applied along the posterior side of the spine.

Although the present embodiment uses a vertically oriented frame or wall on the posterior side of implant 100, in other embodiments, a vertically oriented frame or wall could be located on the anterior side of implant 100. Such an alternative configuration is discussed below and shown in the embodiment of FIGS. 13-15. In still other embodiments, the implant may lack any vertical walls along its perimeter (i.e., along the posterior, anterior or lateral sides).

Generally, the geometry of one or more frame portions of a body (e.g., base portion 200, central keel portion 202 and frame portion 204) could vary from one embodiment to another. For example, frame portions can include one or more windows, slots and/or openings that may facilitate bone growth through implant 100 and/or may reduce weight. In some embodiments, openings in one or more frame portions may provide improved access to the interior region of implant 100, which may facilitate insertion of a bone growth promoting material (BGPM) as discussed in further detail below.

In the embodiment of FIGS. 3-4, base portion 200 may be comprised of a solid outer periphery 225. Additionally, base portion 200 may include a plurality of slots 230 that divide base portion 200 into a posterior segment 232, an anterior segment 234 and a central segment 236. In the embodiment of FIGS. 3-4, each segment intersects central keel portion 202. Moreover, central keel portion 202 may further split slots 230 into a pair of slots separated longitudinally by central keel portion 202. However, in other embodiments, slots 230 could extend through central keel portion 202.

In some embodiments, central keel portion 202 may include openings. In other embodiments, central keel portion 202 could comprise a solid frame with no openings. In some embodiments, providing openings may allow bone growth to occur between opposing lateral sides of the interior of implant 100.

In some embodiments, frame portion 204 could include openings. In other embodiments, frame portion 204 may not include openings. In some embodiments, openings in a frame portion could provide an access point for inserting bone graft material or BGPM into an interior of an implant. The number, size and/or shape of openings in frame portion 204 could vary. In some cases, three or more openings could be used. In other cases, two openings could be used. In still other cases, a single opening could be used. Exemplary shapes for openings that could be used include, but are not limited to: rounded openings, rectangular openings, polygonal openings, regular openings and/or irregular openings. In the embodiment of FIGS. 3-4, frame portion 204 includes four rectangular openings 249. In still another embodiment shown in FIG. 14, a frame portion 704 includes two large oval-shaped windows (i.e., first window 757 and second window 759) that may facilitate insertion of bone graft material (or BGMP) into an interior of the implant.

Some embodiments can include provisions that facilitate implantation, including insertion and/or fixation of the implant. Some embodiments can include a fastener receiving portion. For example, as best seen in FIG. 4, implant 100 includes a fastener receiving portion 238. Fastener receiving portion 238 includes a threaded opening 239 and a reinforced collar 237 to support threaded opening 239. In some embodiments, threaded opening 239 may be configured to receive a tool with a corresponding threaded tip to facilitate implantation of implant 100. In some embodiments, threaded opening 239 may be used with a screw to help attach implant 100 to a bone or another fixation device. In other embodiments, any other features for receiving fasteners and/or implantation tools could be incorporated into implant 100.

Structural Members

An implant may include two or more kinds of structural members. In some embodiments, an implant can include one or more outer structural member, or simply "outer members". Outer members may generally be fully exposed on the outer surfaces of an implant, including along the superior and inferior sides of the implant. The outer members may be configured as bone-contacting members that may contact a vertebra following implantation. In other embodiments, however, some portions of one or more outer members could be hidden or covered by another element along the outer surfaces of the implant.

In some embodiments, an implant can include one or more structural members that provide support to one or more outer members. Such supporting structural members may be referred to as "support members". In some embodiments, at least some portions of each support member may be hidden or covered by an outer member or another element of the implant. Thus, support members may also be characterized as "inner members" as they are generally disposed within the interior of the implant, where the interior may be bounded by the body and the outer members.

Figure 5:
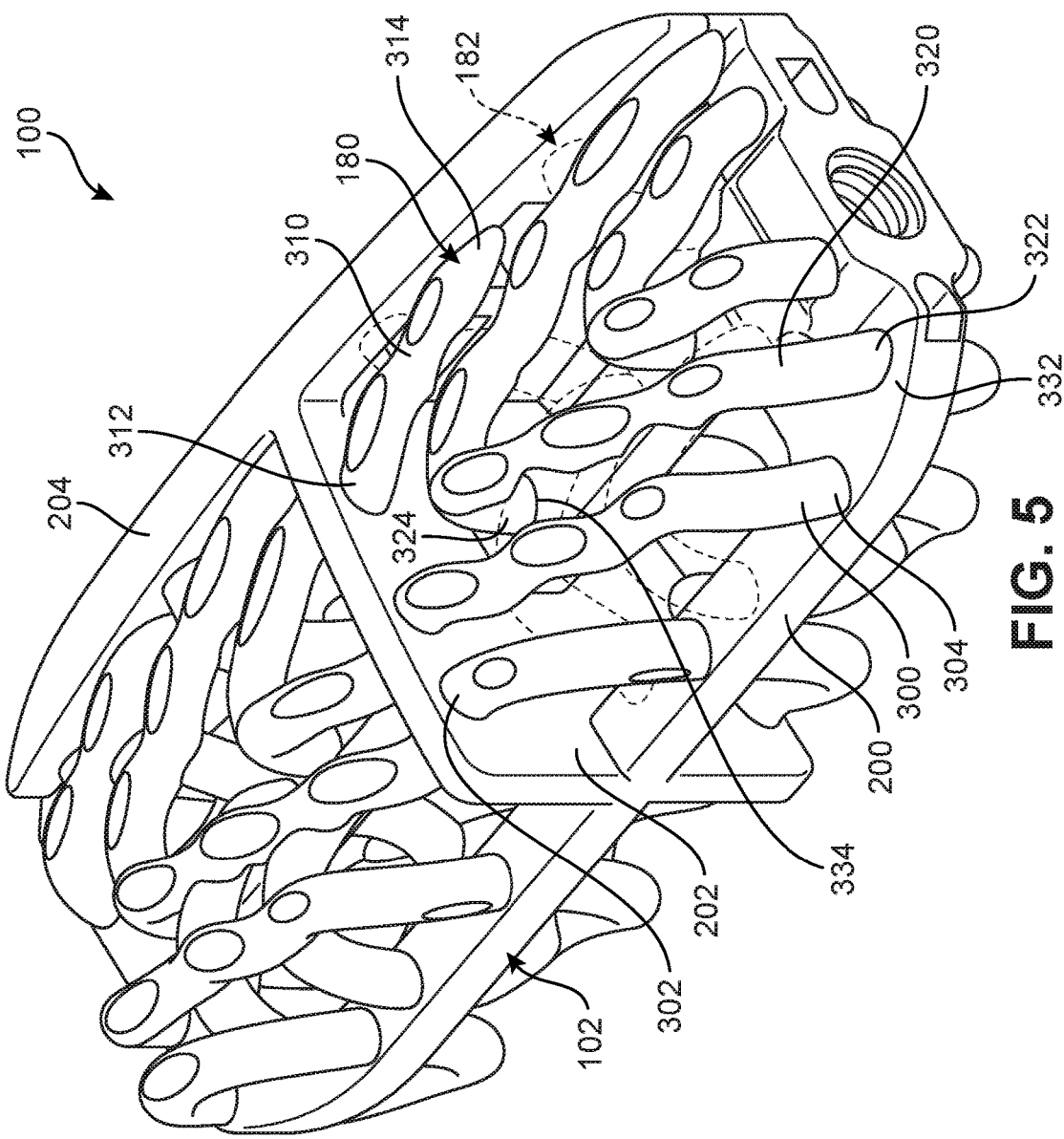
FIG. 5 is a schematic isometric view of an implant with a group of support members shown in phantom, according to an embodiment.
Figure 6:
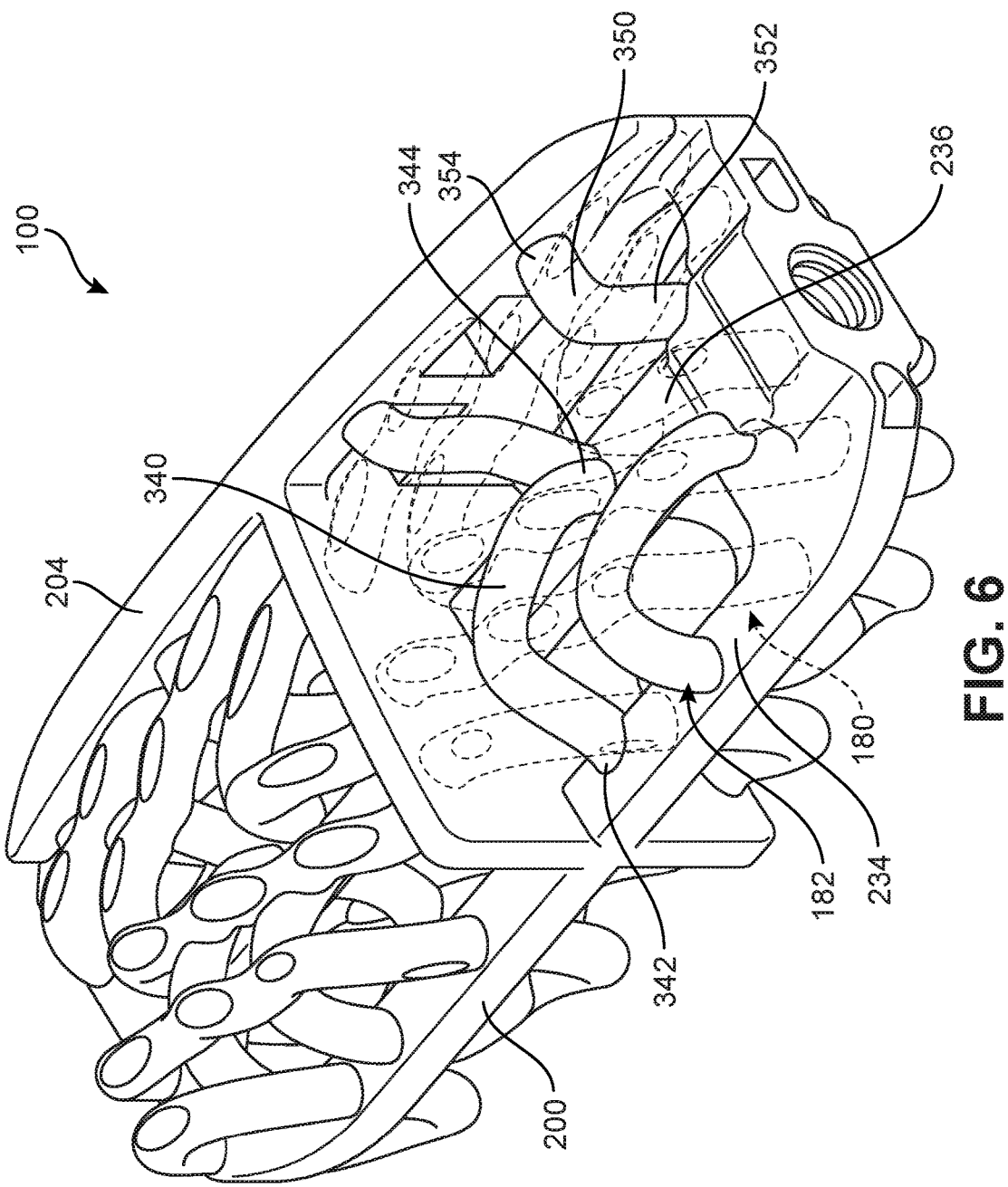
FIG. 6 is a schematic isometric view of the implant of FIG. 5 with a group of outer members shown in phantom.

FIGS. 5 and 6 illustrate schematic isometric views of implant 100, according to embodiment. As seen in FIGS. 5-6, implant 100 may include a plurality of outer members 180 as well as a plurality of support members 182. Outer members 180 can be clearly seen in FIG. 5 where some of support members 182 have been drawn in phantom to more clearly detail the outer members. Likewise, support members 182 can be clearly seen in FIG. 6 where some of outer members 180 have been drawn in phantom to more clearly detail the support members.

Figure 7:
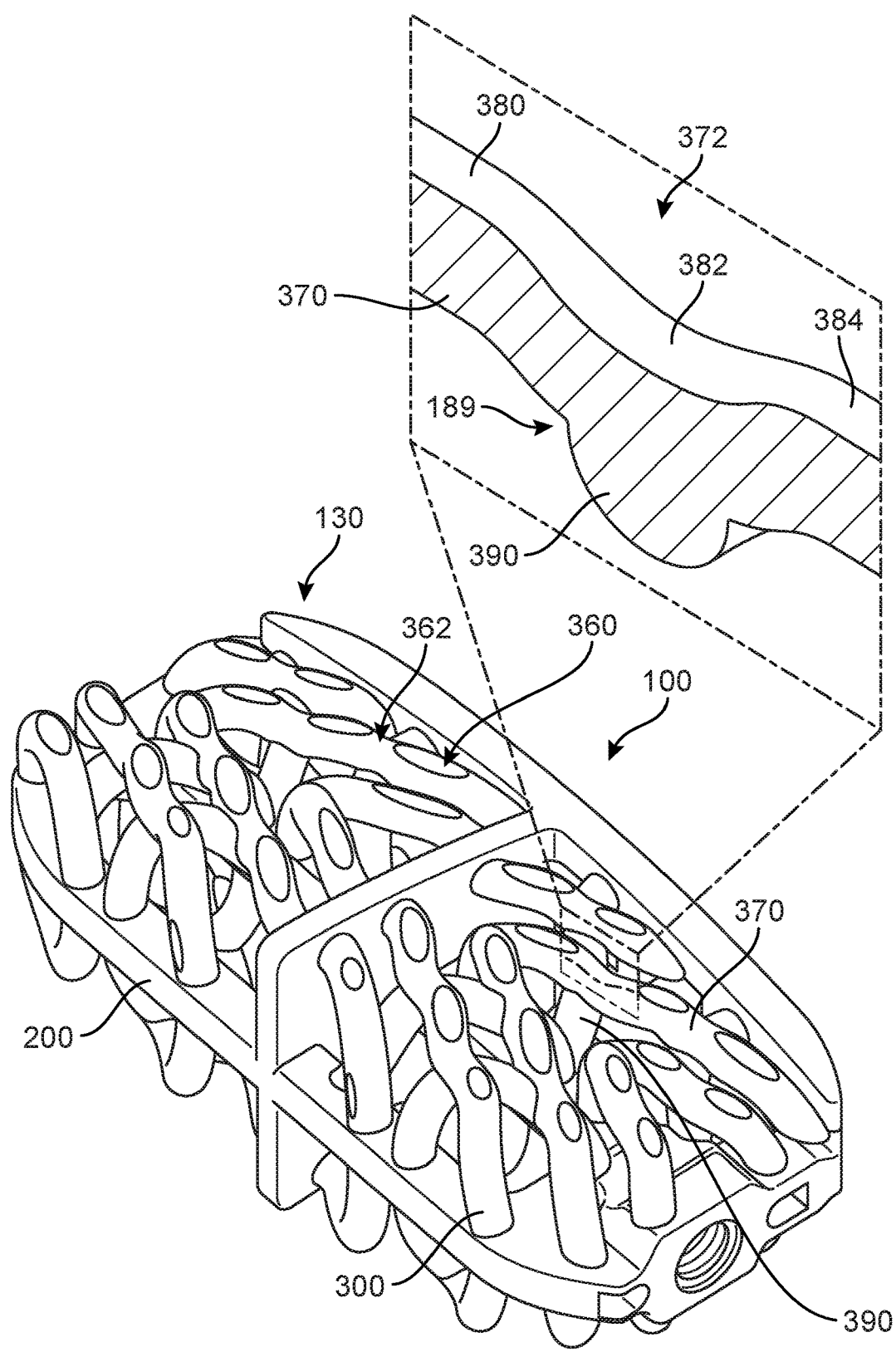
FIG. 7 is an isometric view of an implant including several enlarged cross-sectional views of several structural members, according to an embodiment.

In some embodiments, outer members may be disposed distal to inner members, with outer members generally disposed further outwards along the superior and inferior sides of an implant. Thus, outer members may generally be disposed closer to the vertebral end plates following implantation into the spine. Moreover, at regions where an outer member is attached to an inner member, the attached portion of the outer member may be disposed distal to the attached portion of the inner member. As one example, FIG. 7 illustrates a schematic isometric view of implant 100 including an enlarged cross-sectional view of an attachment region 189 between outer member 370 and support member 390. Here, outer member 370 is seen to extend up and over support member 390. Moreover, outer member 370 is seen to be located distally to support member 390. Here, distally is intended to mean disposed further from base portion 200 or the transverse plane of implant 100.

As best seen in FIGS. 1-2, plurality of structural members 104 may be arranged as four distinct sets that are separated either by base portion 200 or by central keel portion 202. Specifically, plurality of structural members 104 includes a first set of structural members 260, a second set of structural members 262, a third set of structural members 264 and a fourth set of structural members 266. Each set includes both outer members and support members, with the members of each set being attached to base portion 200, central keel portion 202 and/or frame portion 204 in their respective quadrants of implant 100.

Attachment of Structural Members with Body

The following discussion is directed primarily to the first set of structural members 260, however it may be appreciated that similar properties and principles of the specific structural members discussed here may apply to structural members in one of the remaining sets.

In some embodiments, one or more structural members could be closed loops without ends. In other embodiments, at least some structural member comprises two ends. In some cases, structural members with two ends could include one or more ends that are attached to another structural member. In other cases, structural members with two ends could be arranged so that both ends are attached to a portion of a body of an implant. In the exemplary embodiment depicted in FIGS. 5-6, each structural member includes two ends, with each end being attached to some portion of body 102 of implant 100.

In some embodiments, an implant may include at least one outer member with one end attached to a base portion and another end attached to a central keel portion. For example, as seen in FIG. 5, an outer member 300 includes a first end 302 attached to central keel portion 202 and a second end 304 attached to base portion 200.

In some embodiments, an implant may include at least one outer member with one end attached to a frame portion (or sidewall) and another end attached to a central keel portion. For example, as seen in FIG. 5, an outer member 310 includes a first end 312 attached to central keel portion 202 and a second end 314 attached to frame portion 204.

In some embodiments, an implant may include at least one outer member with two ends attached to a base portion of the implant. For example, as seen in FIG. 5, an outer member 320 includes a first end 322 attached to a first portion 332 of base portion 200 and outer member 320 includes a second end 324 attached to a second portion 334 of base portion 200.

In different embodiments, support members could be attached to different portions of a body. In some embodiments, one or more ends of a support member could be attached to a base portion. In other embodiments, one or more ends of a support member could be attached to a central keel portion. In still other embodiments, one or more ends of a support member could be attached to an anterior or posterior frame portion.

In the exemplary embodiment of FIG. 6, many of the support members are attached to base portion 200 at both ends. For example, a support member 340 includes a first end 342 attached to base portion 200 and a second end 344 attached to base portion 200. Other support members are also attached at one end to frame portion 204. For example, a support member 350 includes a first end 352 attached to base portion 200 and a second end 354 attached to frame portion 204.

The particular arrangements for attaching outer members and support members to a body described here may improve utility and strength of the implant. Specifically, by securing one end of some outer members to either a central keel portion or a side frame portion, the total surface area of the outer members that is exposed to adjacent vertebra for fusion can be maximized. Furthermore, by attaching at least some of the support members at both ends to the body, the support members may be made shorter in length and arched so as to improve load-bearing support for the outer members.

The arrangement of structural members with the body may also be designed to achieve a desired total open volume. As used herein a total volume is the combined volume of any openings between structural members, any openings in the body, or between structural members and the body. This open configuration may facilitate bone growth in and through the implant. A portion or all of the open spaces is optionally filled with a bone graft or bone growth promoting material prior to or after insertion of the implant to facilitate bone growth.

The total volume of the open spaces (also referred to simply as the open space volume) within any particular implant is dependent on the overall dimension of the implant as well as the size and dimension of individual components within the implant including structural members, frame portions, etc. The open space volume may range from about 20% to 80% of the volume of the implant. In some embodiments, implant 100 may have an open space volume that is between 25% and 80% of the implant's total volume. In still further embodiments, implant 100 may have an open space volume that is between 40% and 75% of the total implant volume.

Global Symmetries

In some embodiments, an implant can be configured with one or more symmetries. In some cases, an implant may have a mirrored symmetry about one or more reference planes. In other cases, an implant may have a translational symmetry about one or more reference planes. In still other cases, an implant could have both a mirror symmetry and a translational symmetry.

Referring to FIGS. 1 and 2, implant 100 may include at least one mirror symmetry. For purposes of reference, implant 100 may be split into a superior half and an inferior half. Here, the "superior half" of implant 100 includes the portions of body 102 and plurality of structural members 104 disposed above the transverse plane. Likewise, the "inferior half" of implant 100 includes the portions of body 102 and plurality of structural members 104 disposed below the transverse.

With respect to the transverse plane (which coincides generally with base portion 200 in this embodiment), it may be seen that the superior half of implant 100 mirrors the inferior half of implant 100. This includes not only the geometry of the body but also the shape, size and orientations of each structural member. It may be appreciated that this mirror symmetry may only be approximate in some embodiments.

For purposes of reference, implant 100 may be split into a first lateral half and a second lateral half. Referring to FIGS. 1-2, the "first lateral half" includes portions of implant 100 disposed between first lateral edge 270 and central keel portion 202, while the "second lateral half" includes portions of implant 100 disposed between second lateral edge 272.

It may be observed in the embodiment shown in FIGS. 1-2 that the configuration of structural members 104 in the first lateral half is approximately similar to the configuration of structural members 104 in the second lateral half. More specifically, the pattern of structural members 104 repeats through the first lateral half and the second lateral half. In contrast to the pattern of structural members, the geometry of the underlying base portion 200 is mirror symmetric about central keel portion 202, rather than a repeating configuration.

Helical Geometry of Outer Members

Embodiments can include provisions for protecting bone growth along and adjacent to outer members of an implant. In some embodiments, an outer member can be configured with a geometry that helps to protect new bone growth in selected regions or "protected fusion zones". In some embodiments, an outer member can have a spiral, helical or twisted geometry that provide a series of such protected fusion zones for enhanced bone growth.

Some outer members may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Figure 8:
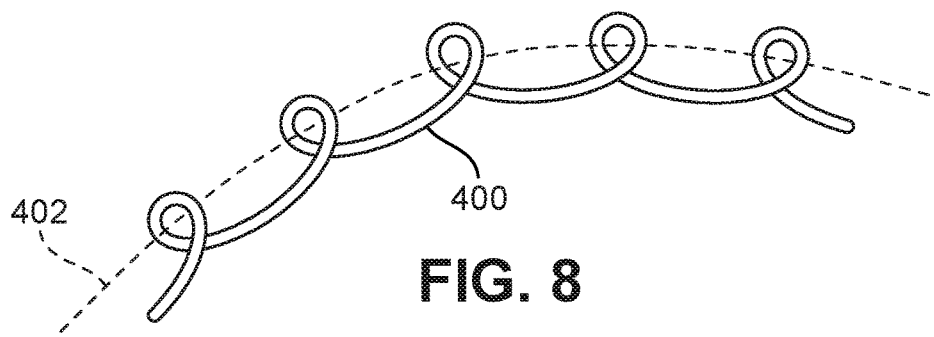
FIG. 8 is a schematic view of a curve with a generalized helical geometry, according to an embodiment.

FIG. 8 illustrates a schematic view of a curve 400 with a generalized helical geometry. Curve 400 is seen to wind around a fixed path 402 that is itself curved. In contrast to curve 400, however, fixed path 402 does not include any turns, windings, etc. An example of a helical curve with a straight fixed path is shown in FIG. 1 of the Coiled Implant Application.

Curves having a generalized helical geometry (also referred to as generalized helical curves) may be characterized by "coils", "turns" or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Figure 9:
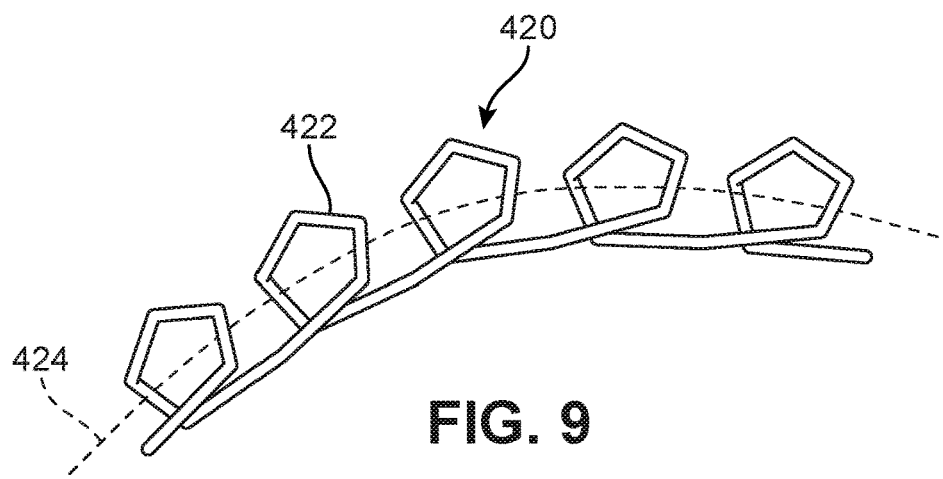
FIG. 9 is a schematic view of another curve with a generalized helical geometry, according to an embodiment.

Generalized helical curves need not be circular or even round. In some embodiments, for example, a generalized helical curve could have linearly-segmented shape (or locally polygonal shape) such that each "coil" or "turn" is comprised of straight line segments rather than arcs or other curved segments. An example of such a generalized helical curve is shown in FIG. 9. Referring to FIG. 9, generalized helical curve 420 is seen to be comprised of straight-line segments 422. The angles between adjacent segments are such that they wind or loop around a fixed path 424 in "polygonal coils".

Figure 10:
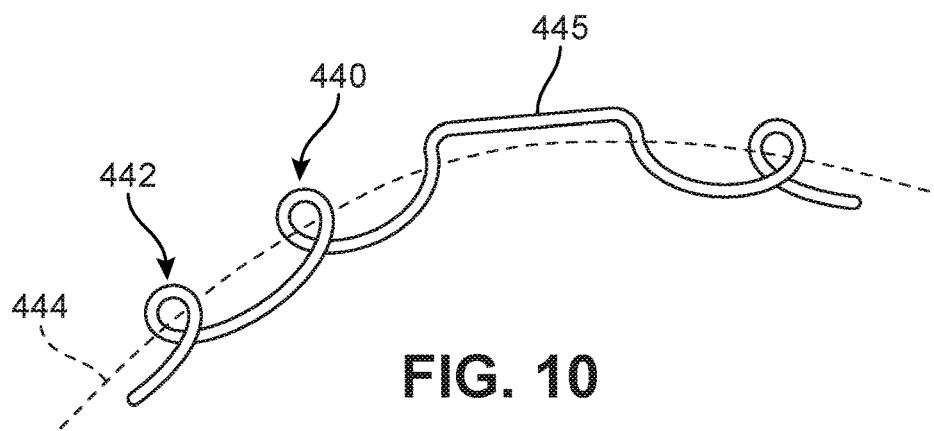
FIG. 10 is a schematic view of a curve with a generalized helical geometry including a straight segment, according to an embodiment.

Generalized helical curves may also include combinations of curved and straight segments. An example of such a combination curve is depicted in FIG. 10. Referring to FIG. 10, generalized helical curve 440 includes generally round (i.e., curved) coil segments 442 curing around a fixed path 444. In addition, curve 440 includes at least one straight-line segment that extends between adjacent coils.

Although the generalized curves shown in FIGS. 8-10 are one-dimensional curves, similar principles may be applied to three-dimensional parts, including structural members.

For purposes of characterizing the geometry of one or more structural members, each structural member can be understood to have a "central member curve". The central member curve of each structural member may be defined as a curve that extends along the length of the structural member such that each point along the curve is centrally positioned within the structural member.

In embodiments where a structural member winds or loops around a fixed path with an amplitude or diameter that is much greater than the cross-sectional diameter of the structural member itself, the structural member may be wound into visible distinct coils. Such coils are discussed in thorough detail in the Coiled Implant Application. In other embodiments, however, a structural member could be wound around a fixed path with an amplitude or diameter that is less than the cross-sectional diameter of the structural member itself. In such a case the resulting geometry of a structural member may appear to be twisted, but the geometry may lack the distinct coils seen in the Coiled Implant Application. However, it may be appreciated that while the outermost surface of such a structural member may not exhibit distinct coils, the central member curve of the structural member does have such coils or turns and moreover has a clear generalized helical geometry.

Figure 11:
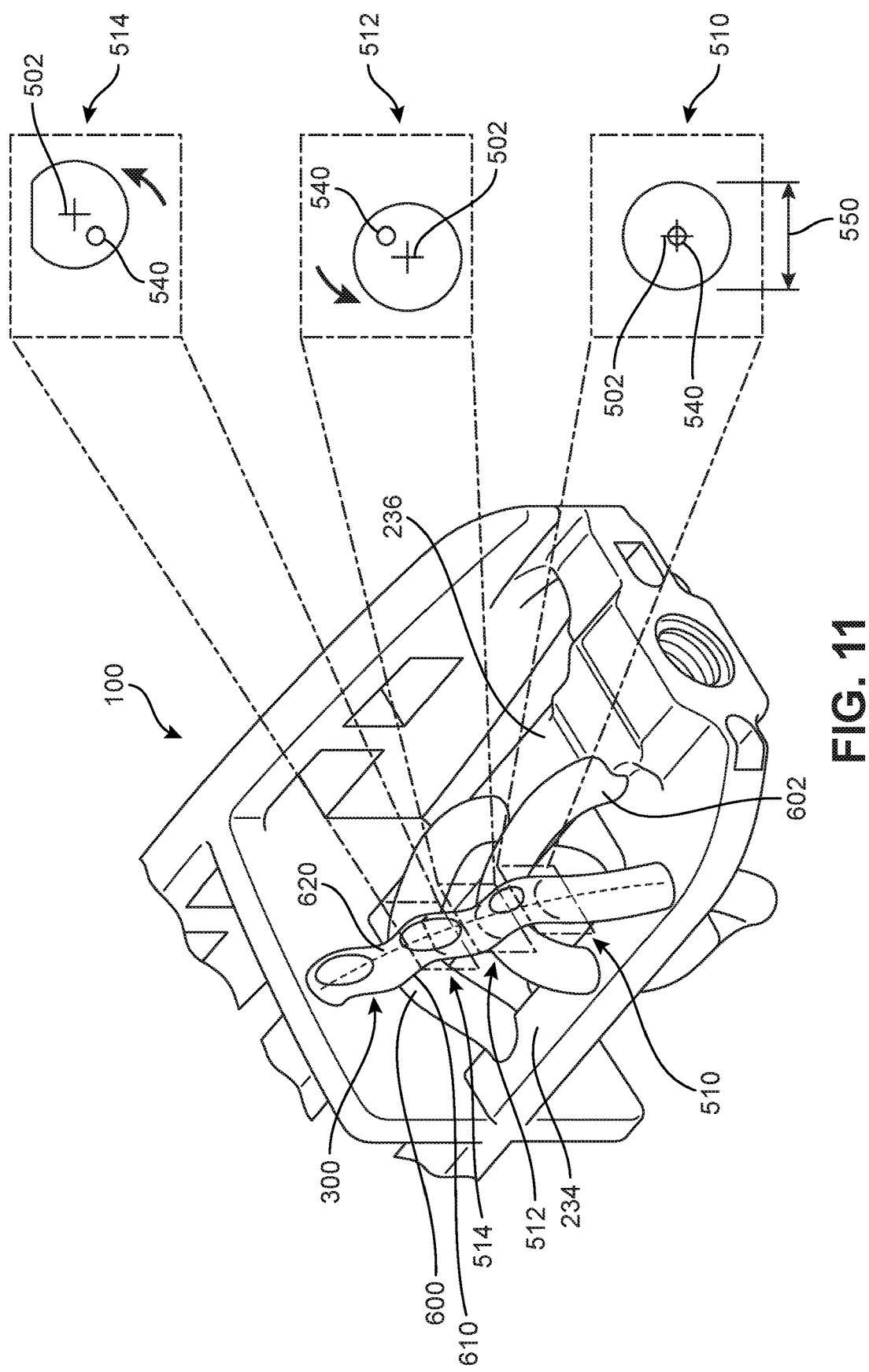
FIG. 11 is a schematic isometric view of a portion of an implant with a few structural members shown in isolation so as to demonstrate the generalized helical geometry of an outer member, according to an embodiment.
Figure 12:
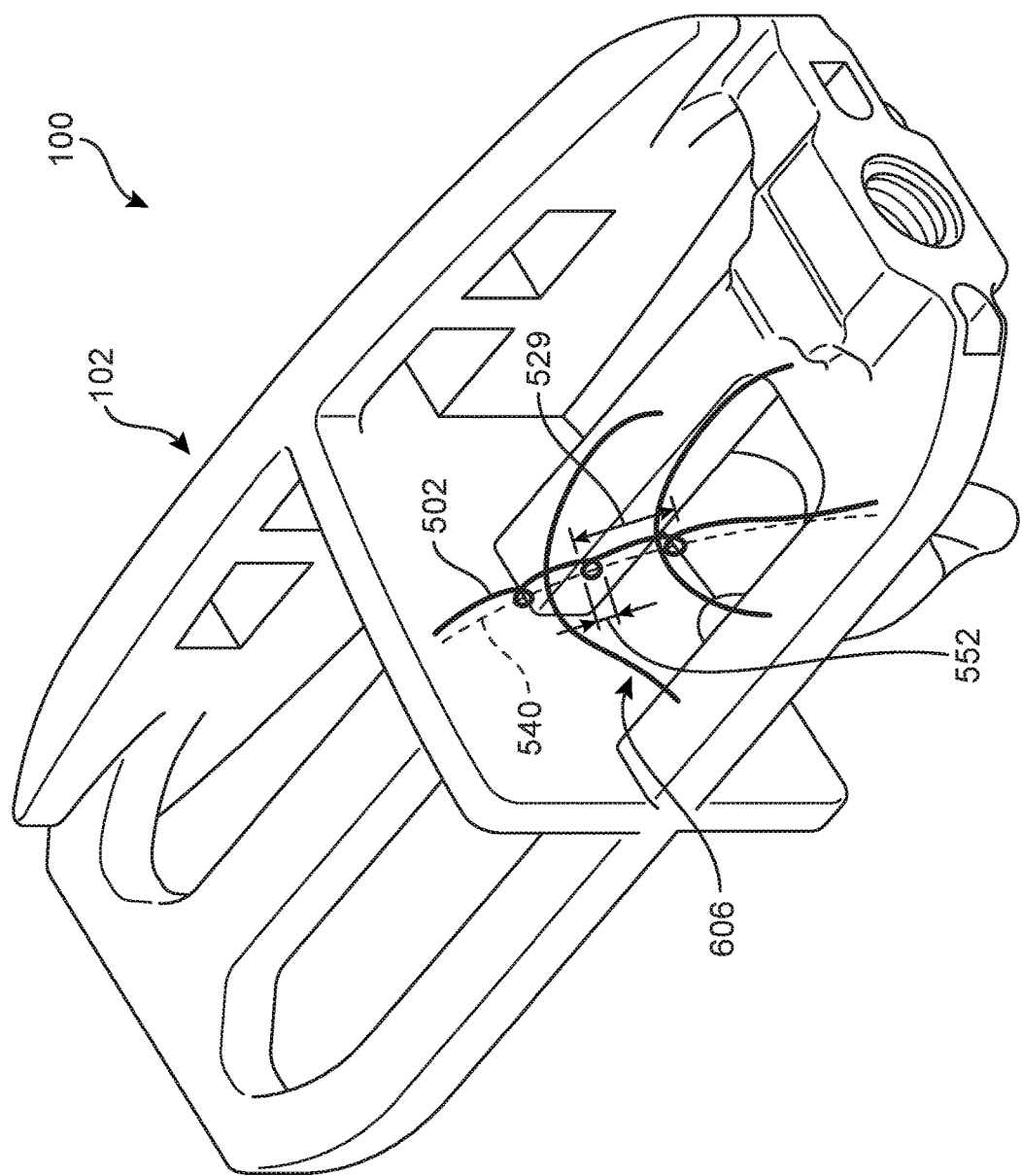
FIG. 12 is a schematic isometric view of the implant of FIG. 11, including the central member curves of the structural members seen in FIG. 11.

FIG. 11 is a schematic isometric view of implant 100 with a single outer member 300 shown. Here, two support members are also visible. The remaining structural members have been removed in FIG. 11 for purposes of clarity. FIG. 12 is a schematic isometric view of body 102 with all structural members removed for clarity.

As seen in FIG. 11, the outer surface of outer member 300 exhibits a twisted geometry indicative of a spiral or helix. However, since the winding occurs with an amplitude much smaller than the thickness of outer member 300, the geometry of the part may be difficult to discern. The generalized helical geometry of outer member 300 becomes much clearer when the geometry of its central member curve 502 (which is clearly seen in FIG. 12) is considered as it winds around a fixed path 540 (also shown in FIG. 12).

For purposes of illustrating the winding geometry of outer member 300, FIG. 11 includes a sequence of cross-sectional views taken along outer member 300. In a first cross-sectional view of a first portion 510, a first point (indicated using a cross in FIG. 11) of central member curve 502 is seen to be approximately aligned with a corresponding point (indicated using a circle) of fixed path 540. At a second portion 512, a second point of central member curve 502 is seen to be positioned at a first rotational position away from a corresponding point of fixed path 540. At a third portion 514, a third point of central member curve 502 is seen to be positioned at a second rotational position from a corresponding of fixed path 540. Thus, it can be seen that as outer member 300 twists with a small amplitude along its extension between base portion 200 and central keel portion 202, central member curve 502 indeed winds or spirals around fixed path 540. Here, it may be understood that fixed path 540 represents the "average" or approximate path of outer member 300 that ignores the helical deviations at some segments.

As clearly seen in comparing FIGS. 11 and 12, the cross-sectional diameter 550 of outer member 300 is greater than a corresponding winding diameter 552 of the coils or turns in central member curve 502. In other embodiments, the cross-sectional diameter of an outer member could be less than a corresponding winding diameter of the coils or turns of its central member curve. In such an embodiment, the outer member would be configured in a series of distinct coils.

Referring to FIGS. 11 and 12, outer member 300 does not have a generalized helical geometry through its entire length. Instead, its central member curve is configured with a winding segment where the central member curve completes several full turns (three in FIGS. 11-12) around a fixed path. Away from the winding segment, its central member curve may not include any turns, twists, etc.

Although the present embodiment includes at least one outer member with a winding segment that makes one or more full turns around a fixed path, other embodiments could be configured with central member curves that only make partial turns around a fixed path.

While the description here has focused on the geometry of a single outer member 300, it may be appreciated that some or all of the remaining outer members in plurality of structural members 104 may have a similar generalized helical geometry. It may be further appreciated that two different outer members could have slightly different geometries, with distinct outer member curves that include variations in the number of windings, shape of the windings, etc.

In some embodiments, an implant can include outer members that are locally helical over small distances compared to the length, width or height of the implant. For example, implant 100 may be characterized as having outer members that are locally helical or locally spiraling, rather than globally helical. In particular, each outer member of implant 100 is bounded within a single quadrant of implant 100 and does not cross the transverse plane or the median plane of implant 100. Thus, a full turn of the outer members is accomplished over distances that are much smaller than half the length, width or height of the implant. This allows multiple windings within each quadrant of the implant and also results in the pitch between windings being smaller than the length, width or height of the implant. For example, in FIG. 12, central member curve 502 has a pitch 529 between adjacent windings or turns that is less than one third of the length of outer member 300. Pitch 529 is also less than one tenth of the length of implant 100. This relatively small pitch size allows for a greater number of proximal surface regions along each outer member, thereby increasing the number of available protected fusion zones of the inferior and superior surfaces of implant 100.

In some embodiments, the helix-like geometry of outer members provides distinct regions exposed on the superior and inferior sides of an implant. For example, referring back to FIG. 7, each outer member includes one or more distal regions 360 that may be seen as 'peaks' in the outer member along the superior side 130 of implant 100. In at least some embodiments, these distal regions 360 may be flattened or "smoothed" so as to provide a flat or smooth distal-most surface on superior side 130 (and inferior side 140), thereby facilitating contact with adjacent vertebrae. See, for example, FIG. 15 which shows another embodiment of an implant where the approximately smooth superior and inferior surfaces of the implant can be seen. In other embodiments, a distal surface region may be curved. In some cases, the distal surface region could have a curvature that matches the curvature of the adjacent surface regions of the outer member. In other cases, the distal surface region could have a different curvature (e.g., more convex) than adjacent surface regions of the outer member.

Outer members may also include proximal regions 362 that may be seen as 'valleys' in the outer member along the superior side 130 of implant 100. Whereas the distal regions 360 may directly come into contact with the vertebrae during and following implantation of implant 100, proximal regions 362 may be recessed or spaced apart from direct contact with the vertebrae, at least before new bone growth has developed.

As a particular example, FIG. 7 includes an enlarged cross-sectional view of a portion of an outer member 370 and underlying support member 390. Specifically, an outwardly facing surface portion 372 of outer member 370 is visible. As used herein, the "outwardly facing surface portion" of an outer member is the portion of the surface of the outer member facing towards a vertebra during implantation, or facing away from an interior of the implant. Outwardly facing surface portion 372 includes a first distal surface region 380, a proximal surface region 382 and a second distal surface region 384. As discussed in further detail below, this local geometry provides a series of protected fusion zones adjacent each proximal surface region, where new bone growth can be protected during early bone fusion.

Arch-Like Geometry of Support Members

While outer members may have generalized helical geometries, the geometries of the support members may be selected to enhance strength and support. In some embodiments, support members could have a generally tube-like (solid) shape and may extend in simple curves from one portion of a body to another. In particular, in some cases, the central member curve of a support member may be smoothly curved without any local twists, windings or coils.

Referring to FIG. 11, the support members of the present embodiment are generally tube-like in shape and extend in simple curves from one portion of body 102 to another. For example, support member 600 and support member 602 both extend in an arc-like shape from anterior segment 234 to central segment 236 of base portion 200. Moreover, as seen in FIG. 12, the central member curves 606 of these support members do not include windings, coils or twists about a fixed curve.

Thus, it may be appreciated, that in some embodiments, support members may generally be shorter and their geometry may be more arch-like to improve strength and provide increased support for the outer members. In contrast, the outer members may generally have a longer length and may be less arch-like in shape relative to the support members, as the outer members need to extend across as much of the superior/inferior sides of an implant as possible to provide contact with the vertebrae.

While some embodiments include outer members with generalized helical geometries and inner support members with arch-like geometries, in other embodiments any structural member could be configured with any type of geometry. For example, in another embodiment, one or more inner support members could have a generalized helical geometry. In still another embodiment, one or more outer members could have an arch-like geometry.

Support at Proximal Regions

In different embodiments, the attachment between a support member and an outer member could occur at various locations. In some embodiments, a support member could be attached near a distal surface region along the outer surface of an outer member. In other embodiments, a support member could be attached near a proximal surface region along the outer surface of an outer member.

In some embodiments, each support member is configured to attach to a corresponding outer member at a location adjacent (or underlying) a proximal surface region of the outer member. For example, as shown in FIG. 11, an attachment portion 610 of support member 600 is attached to outer member 300 at a location corresponding to proximal surface region 620 of outer member 300. Likewise, every other support member of implant 100 attaches to one or more outer members only at locations corresponding to proximal surface regions.

This configuration provides for protected fusion zones that encompass the space immediately adjacent the proximal regions. The protected fusion zones are locations along the superior/inferior surfaces of an implant where new bone growth can be partially protected from forces applied to the outer members by adjacent support members or directly from a vertebra.

Figure 20:
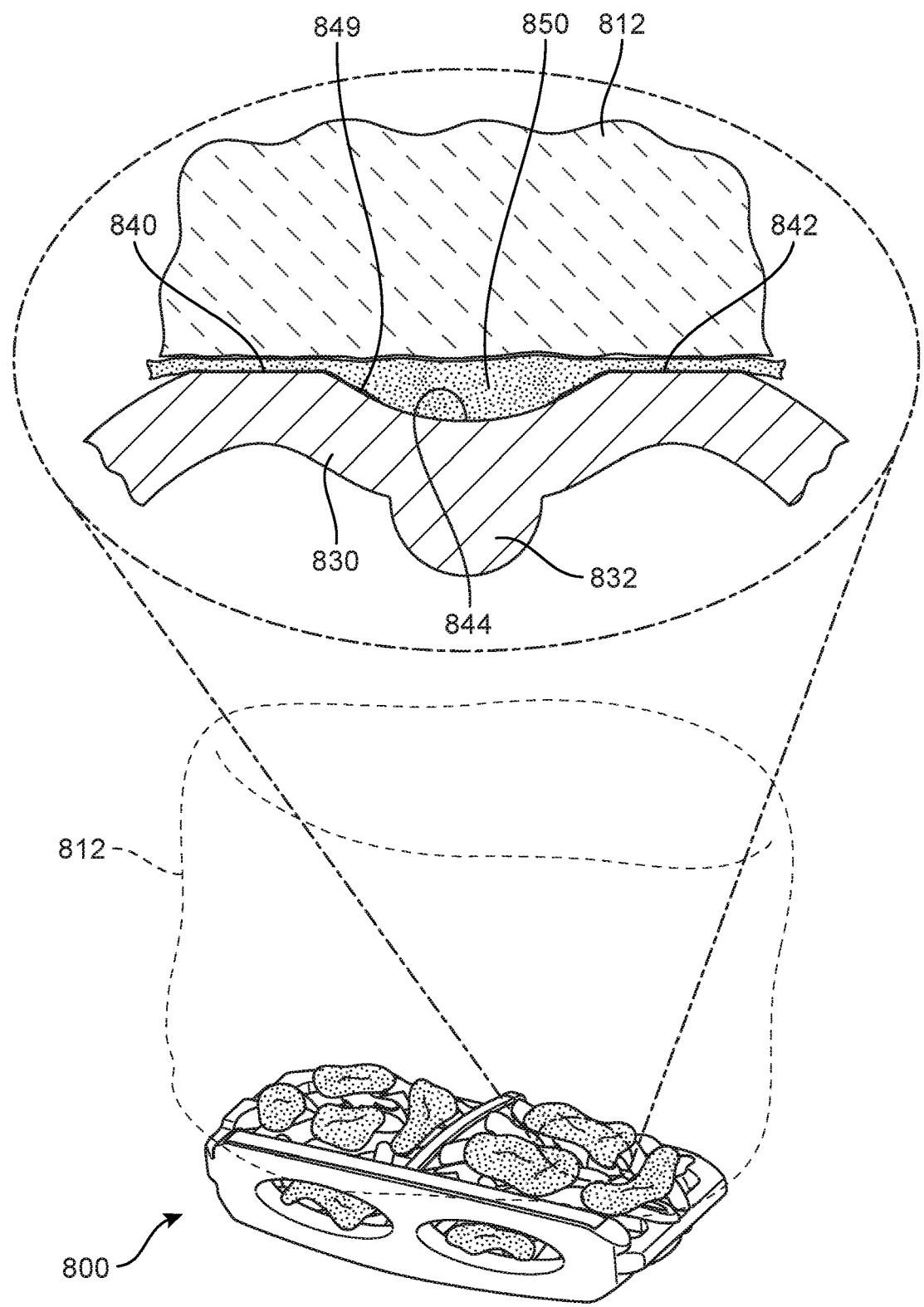
FIG. 20 is a schematic view depicting a protected fusion zone formed between a vertebra and an outer member, according to an embodiment.
Figure 21:
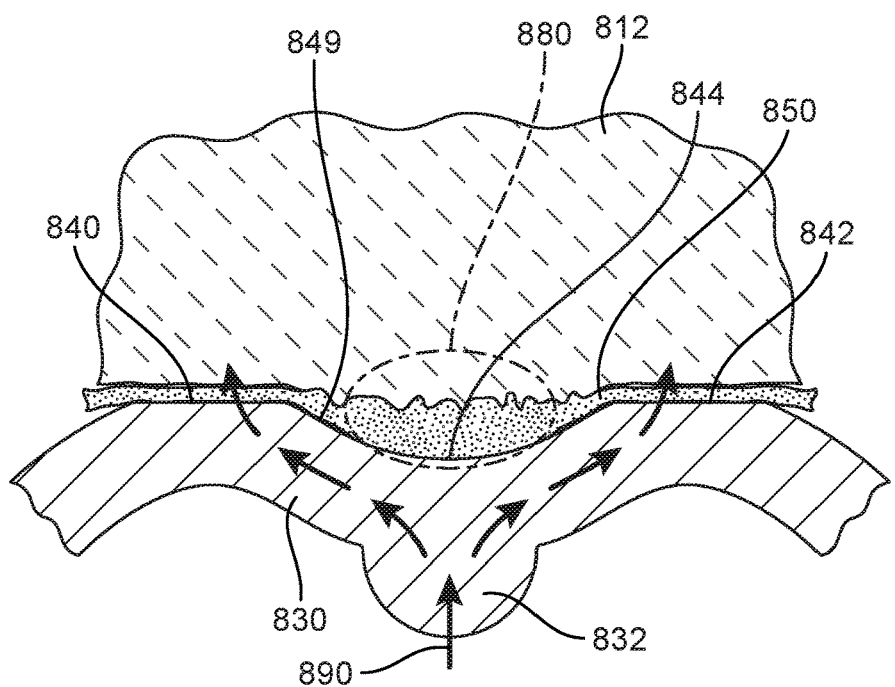
FIG. 21 is a schematic view depicting bone growth into the protected fusion zone of FIG. 20, according to an embodiment.
Figure 22:
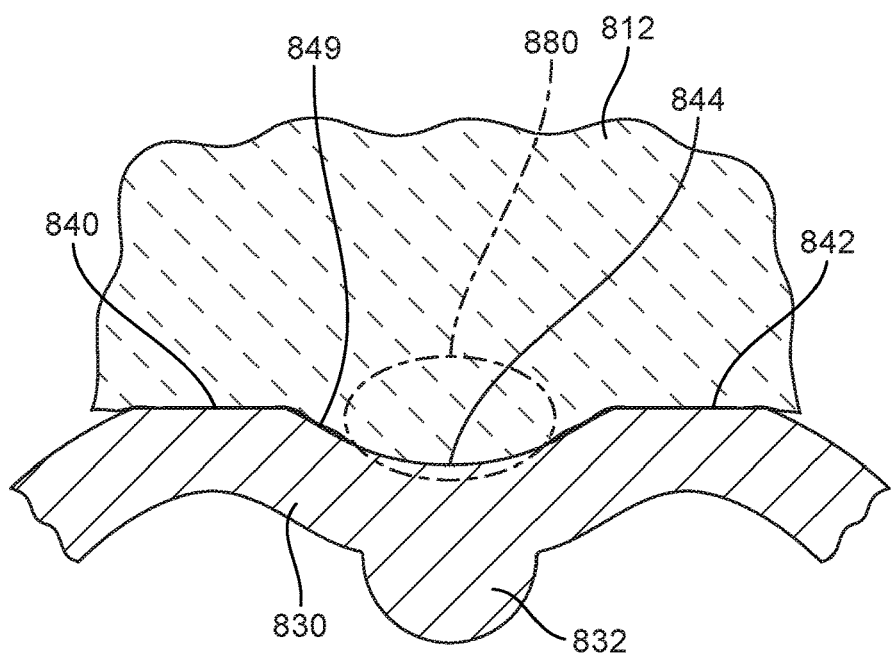
FIG. 22 is a schematic view of bone growth in the protected fusion zone of FIG. 21.

By configuring one or more outer members with at least one helical portion, the outer member may provide one or more protected fusion zones on the superior and inferior sides of an implant. These protected fusion zones encompass the space immediately adjacent the proximal regions of the outer members. The recessed spaces provided by the proximal regions allow for pockets of new bone growth adjacent initial fusion that may occur at the distal regions. Moreover, because the support members are attached near the proximal surface regions, and not at the distal surface regions, forces applied to the outer members by either the support members or by a vertebra can be directed away from the protected fusion zones, thereby minimizing the disturbance of new bone growth. A demonstration of bone growth within a protected fusion zone is shown in FIGS. 20-22 and discussed below.

Alternative Embodiment with Surface Texturing

Figure 13:
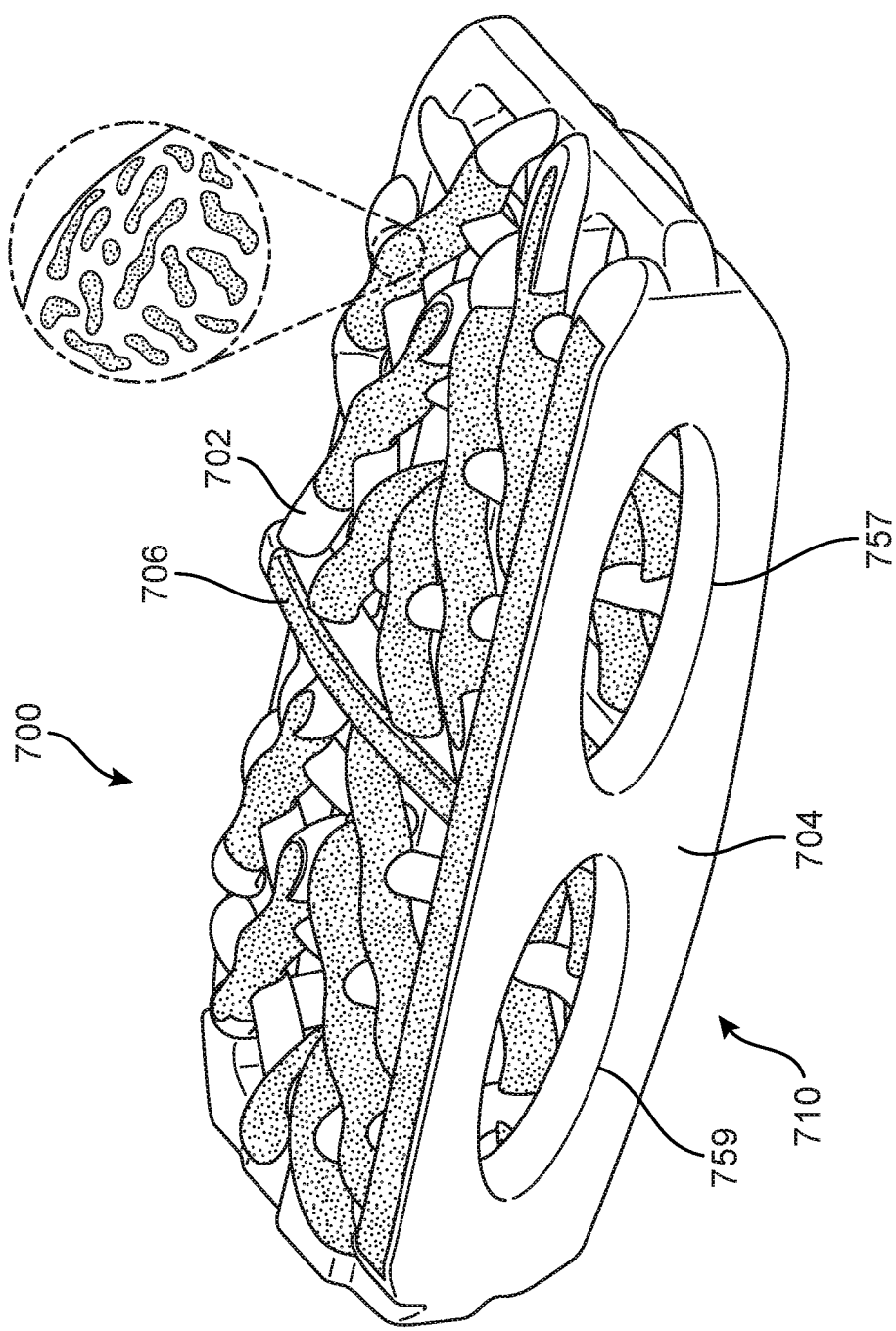
FIG. 13 is a schematic view of another embodiment of an implant having a textured surface in one or more regions.

Embodiments can include provisions for texturing one or more surfaces of an implant. Such texturing can increase or otherwise promote bone growth and/or fusion to surfaces of the implant. In some embodiments, outer members may be textured while support members may not be textured. This helps initial bone growth to be directed along the outer members and especially into the protected fusion zones, rather than growing initially across support members. In other embodiments, however, support members could include surface texturing. In still further embodiments, one or more surfaces of a body could include surface texturing. Referring to FIG. 13, one embodiment of an implant 700 may include surface texturing on outer members 702 as well as the inferior and superior surfaces a side frame portion 704 and central keel portion 706.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. In some embodiments, the roughness can be created by 3D printing a raised pattern on the surface of one or more regions of an implant. In some embodiments, the resulting roughened surface may have pores of varying sizes. In some embodiments, pore sizes could range between approximately 0.2 mm and 0.8 mm. In one embodiment, pore sizes could be approximately 0.5 mm. Of course in other embodiments, surface roughness comprising pore sizes less than 0.2 mm and/or greater than 0.8 mm are possible.

Implant 700 may include similar provisions to implant 100 discussed above. For example, implant 700 can include a body portion and a plurality of structural members. In some cases, the body portion may include a side frame portion 704. In the embodiment of FIG. 13 side frame portion 704 is located on an anterior side 710 of implant 700, rather than on a posterior side.

Bi-Convex Geometry

Figure 14:
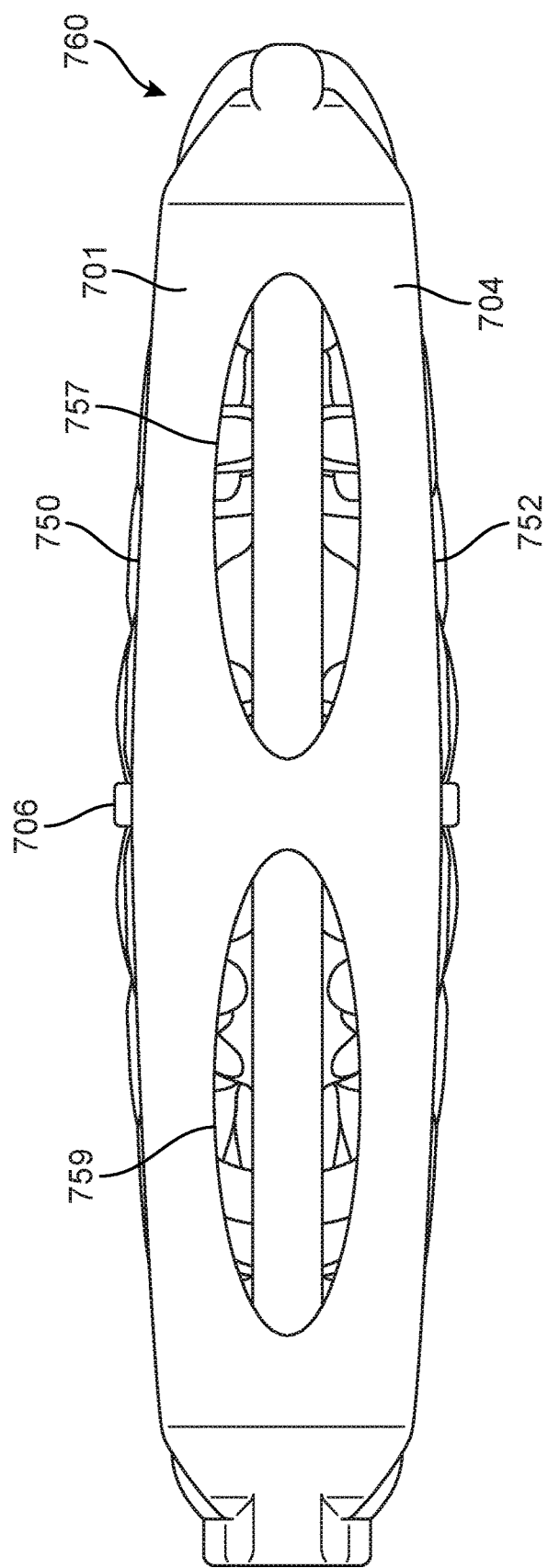
FIG. 14 is a schematic anterior view of the implant of FIG. 13.
Figure 15:
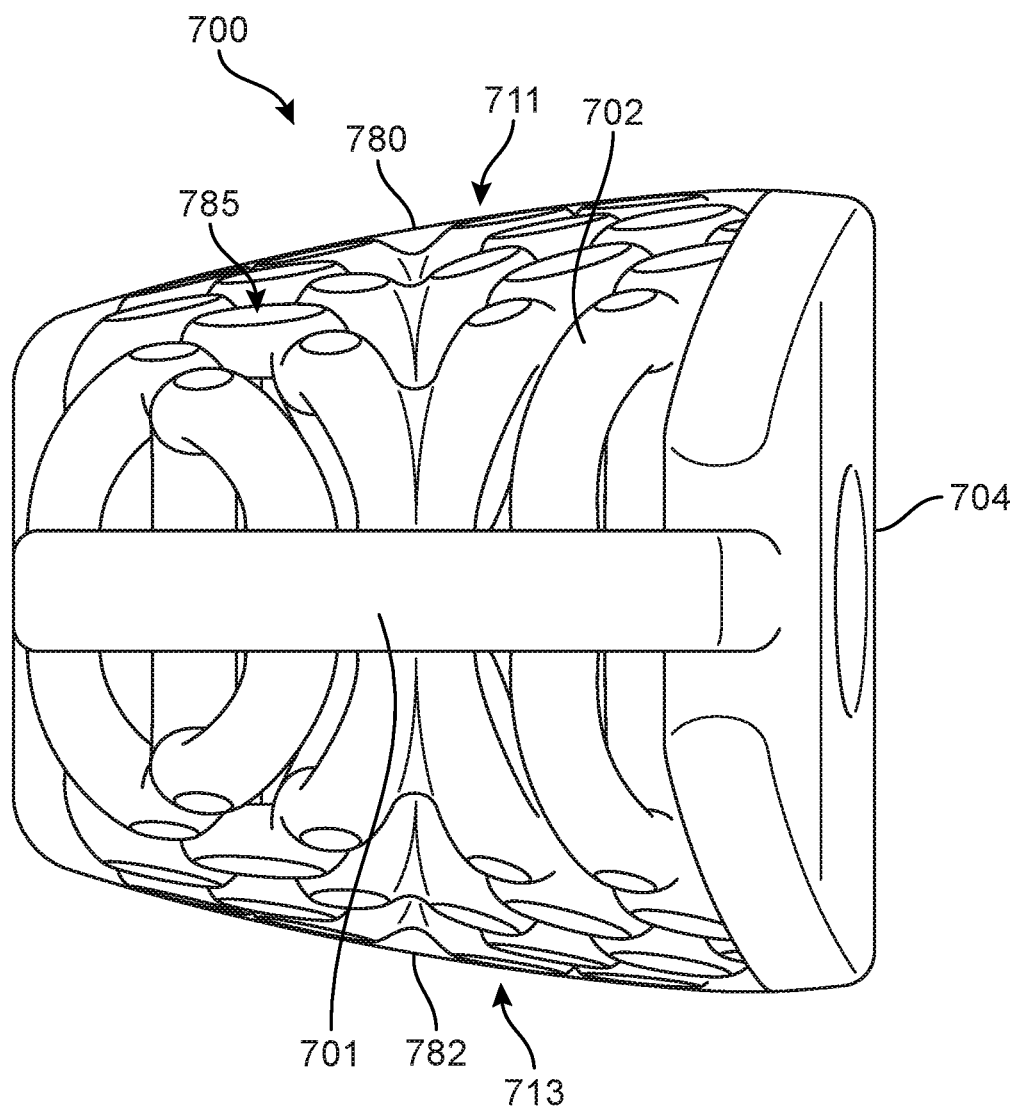
FIG. 15 is a schematic lateral side view of the implant of FIG. 13.

FIGS. 14 and 15 provide anterior side and lateral side (or lateral end) views, respectively, of implant 700. As seen in FIGS. 14-15, implant 700 may be configured with a bi-convex geometry. Specifically, frame portion 704 can be seen to have a convex superior side edge 750 and a similarly convex inferior side edge 752. Furthermore, when viewed from the lateral end shown in FIG. 15, implant 700 has an approximately convex shape along the superior side and the inferior side. In some cases, central keel portion 706 can be configured with a superior edge 780 and an inferior edge 782 that are also convex. Thus, it may be seen that implant 700 is convex in both the longitudinal and lateral directions, which helps to match the geometry of the vertebral endplates. Thus arranging the implant so as to have a convex outer surface on the superior and inferior sides helps to ensure that distal surfaces 785 (i.e., "flattened surfaces") contact the concave surfaces of opposing vertebral plates. In other embodiments, however, the inferior and/or superior surfaces of an implant could be concave, flat, tapered/angulated to provide lordosis or kyphosis, etc. in shape.

In some embodiments, at least one lateral side of an implant may be shaped to facilitate easy insertion. As best seen in FIGS. 14-15, by virtue of the tapered geometry of body 701 and tapered arrangement of structural members 702, lateral side 760 is configured as a rounded end to improve ease of insertion. In some cases, this may be referred to as a "bulleted nose" configuration.

Implantation

Figure 16:
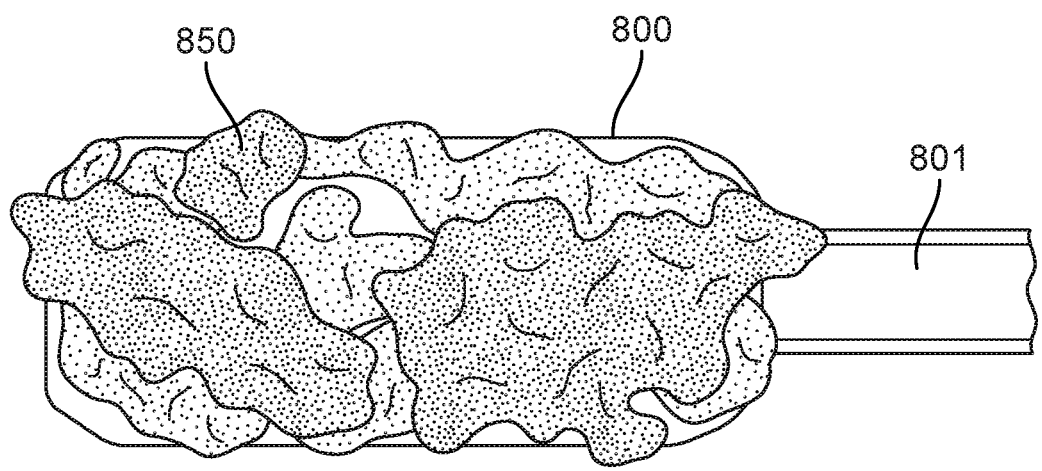
FIG. 16 is a schematic view depicting an implant attached to an implant tool, and where the implant is covered with a bone growth promoting material, according to an embodiment.
Figure 17:
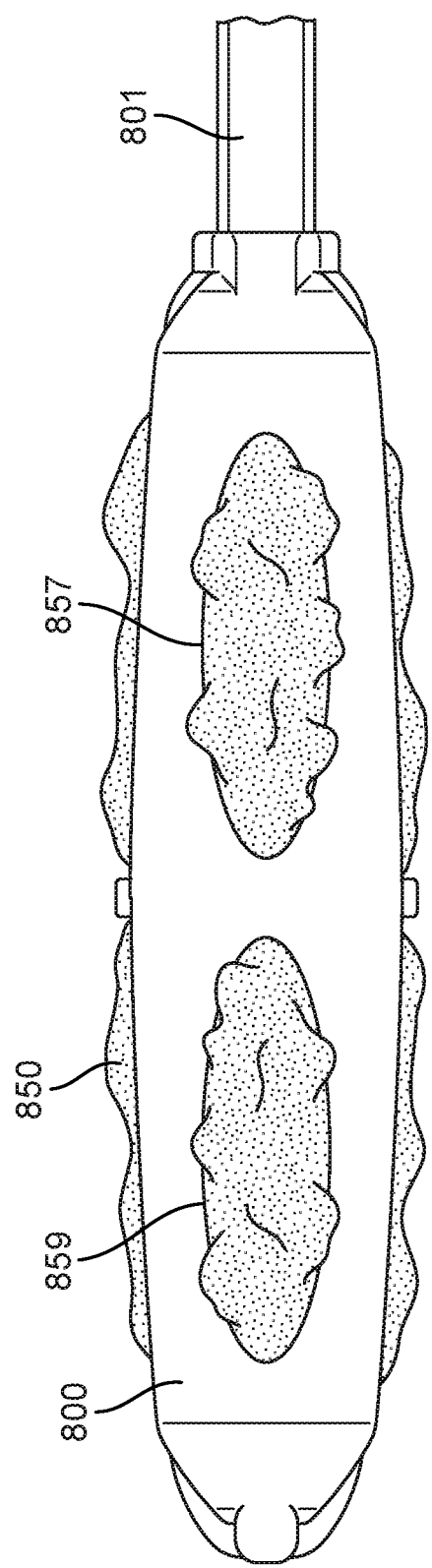
FIG. 17 is a schematic view of the implant of FIG. 16 as viewed on the anterior side.

FIGS. 16-19 illustrate various schematic views of a process of implanting an implant 800. Referring first to FIGS. 16-17, the implantation process may begin with the application of a bone growth promoting material, also referred to as a BGPM, to the implant. As used herein, a "bone growth promoting material" is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant. As seen in FIGS. 16-17, a BGPM 850 has been placed inside an interior of implant 800 and also applied on superior and inferior surfaces of implant 800. Moreover, as shown in FIG. 17, BGPM 850 has been inserted through (and extends through) a first window 857 and a second window 859 of implant 800.

Figure 18:
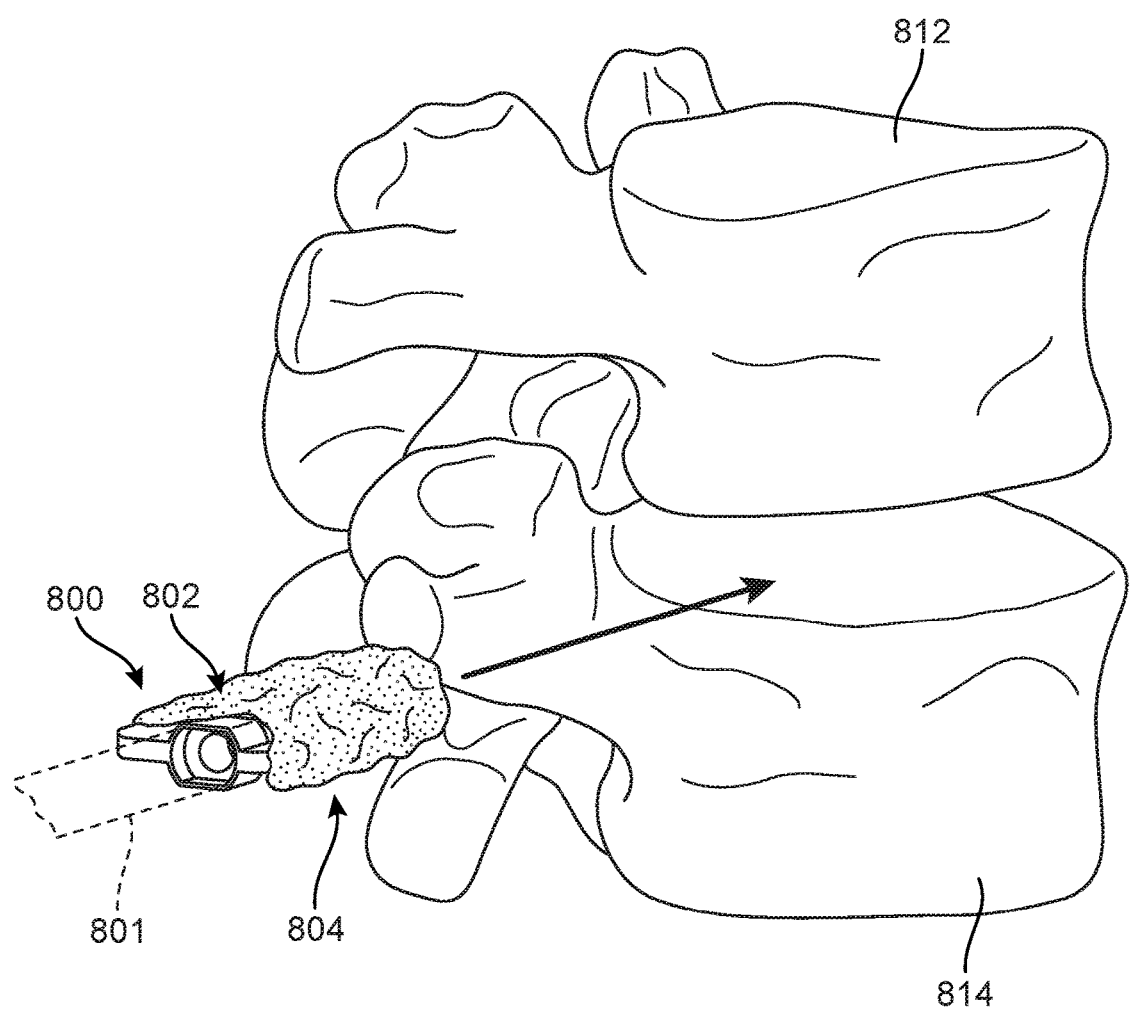
FIG. 18 is a schematic isometric view of an implant being positioned for insertion between two vertebrae, according to an embodiment.
Figure 19:
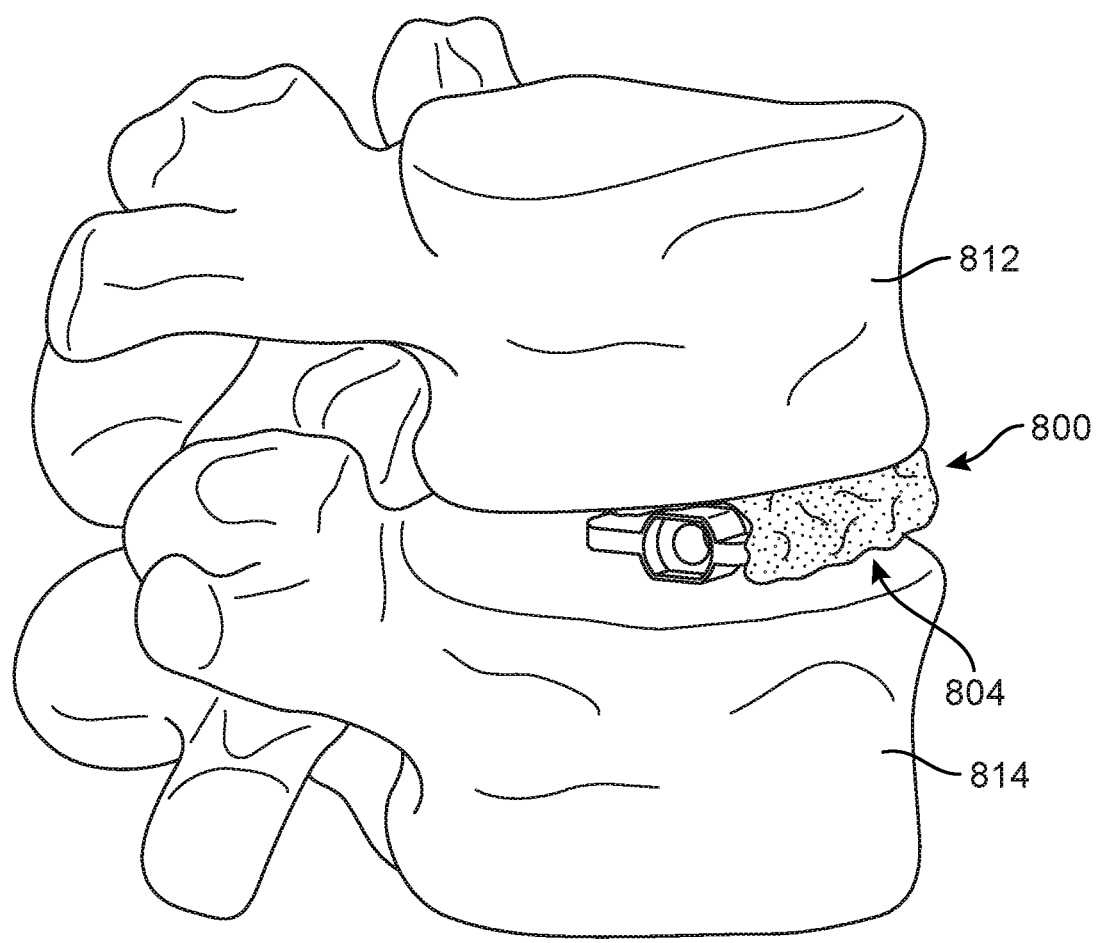
FIG. 19 is a schematic isometric view of the implant of FIG. 18 inserted between the two vertebrae.

FIGS. 18 and 19 show schematic views of the implant pre-implantation (FIG. 18) and post-implantation (FIG. 19). Once implanted, implant 800 may be disposed between, and in direct contact with, adjacent vertebra. Specifically, a superior side 802 of implant 800 is disposed against first vertebra 812. Likewise, an inferior side 804 of implant 800 is disposed against second vertebra 814.

In different embodiments, implantation methods could vary. In some embodiments, implant 800 may be secured to an implantation tool 801 (partially seen in FIGS. 16-18) that is used to drive implant 800 into the spine. Implantation tool 801 could be any rod, ram, pole or other device that can be hammered, rammed, or otherwise driven to position implant 800 between adjacent vertebrae. As previously mentioned, in some cases, an implantation tool could be attached to implant 800 at a fastener receiving portion (i.e., a threaded opening for receiving a threaded shaft from a tool).

FIGS. 20-22 depict a sequence of bone growth along implant 800. More specifically, FIGS. 20-22 show an enlarged schematic view of a section of an outer member 830 (as seen from the side) and a support member 832 (as seen head on) in relation to vertebra 812. Initially, a first distal surface region 840 and a second distal surface region 842 of outer member 830 are disposed adjacent vertebra 812. In some cases, the distal surface regions may be in direct contact with the vertebra. In other cases, a layer of BGPM may be disposed between the distal surface regions and the vertebra. As seen in the embodiment of FIG. 20, a layer of BGPM 850 is disposed between first distal surface region 840 and vertebra 812 as well as between second distal surface region 842 and vertebra 812 to help promote bone growth and fusion at these locations. Furthermore, BGPM 850 extends throughout the region between vertebra 812 and proximal surface region 844.

Initial bone fusion and growth may occur along these regions, as seen in FIG. 21. With time, bone growth may proceed along the outwardly facing surface portion 849 of outer member 830, including growth towards proximal surface region 844 and into the protected fusion zone 880 bounded by vertebra 812 and the outwardly facing surface portion 849 of outer member 830. As seen in FIG. 21, in some cases, vertebra 850 may begin to partially fuse with BGPM 850 in the protected fusion zone 880.

Using this configuration, the new bone growth occurring in protected fusion zone 880 may be protected from local forces between outer member 830 and vertebra 812. Specifically, FIG. 21 shows a force 890 that has been applied by support member 832 to outer member 830. As seen here, the generalized helical shape of outer member 830, which provides the protected fusion zone 880, helps to direct the applied forces outwardly and up to the distal regions (distal surface region 840 and distal surface region 842) and away from the new bone growth disposed in protected fusion zone 880. This helps minimize the disturbance to new bone growth occurring in the protected fusion zone 880. It may be appreciated that this structural configuration may also help direct any forces applied by the vertebra to an outer member from the distal surface regions to the proximal surface region while bypassing the protected fusion zone.

In FIG. 22, new bone growth in protected fusion zone 880 has been formed and fused with proximal surface region 844. In some embodiments, the new bone growth may have sufficient strength to support loads, including vertical or compressive loads. In other words, protected fusion zone 880 provides a zone for new bone growth to develop until the bone has fully fused and can become a load bearing structure.

Figure 23:
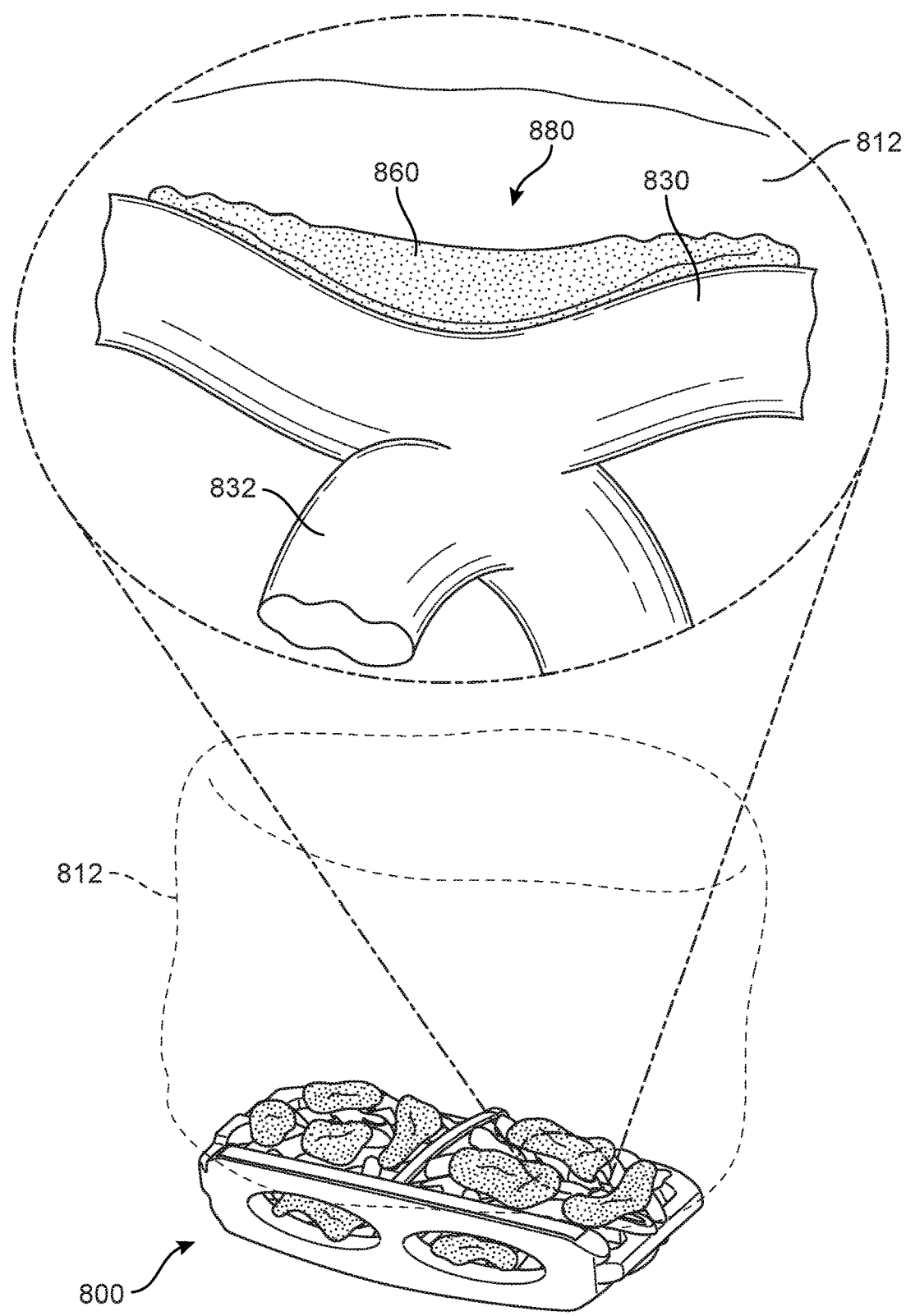
FIG. 23 is a schematic isometric view of an implant with an enlarged view of a protected fusion zone with a portion of bone growth promoting material, according to an embodiment.
Figure 24:
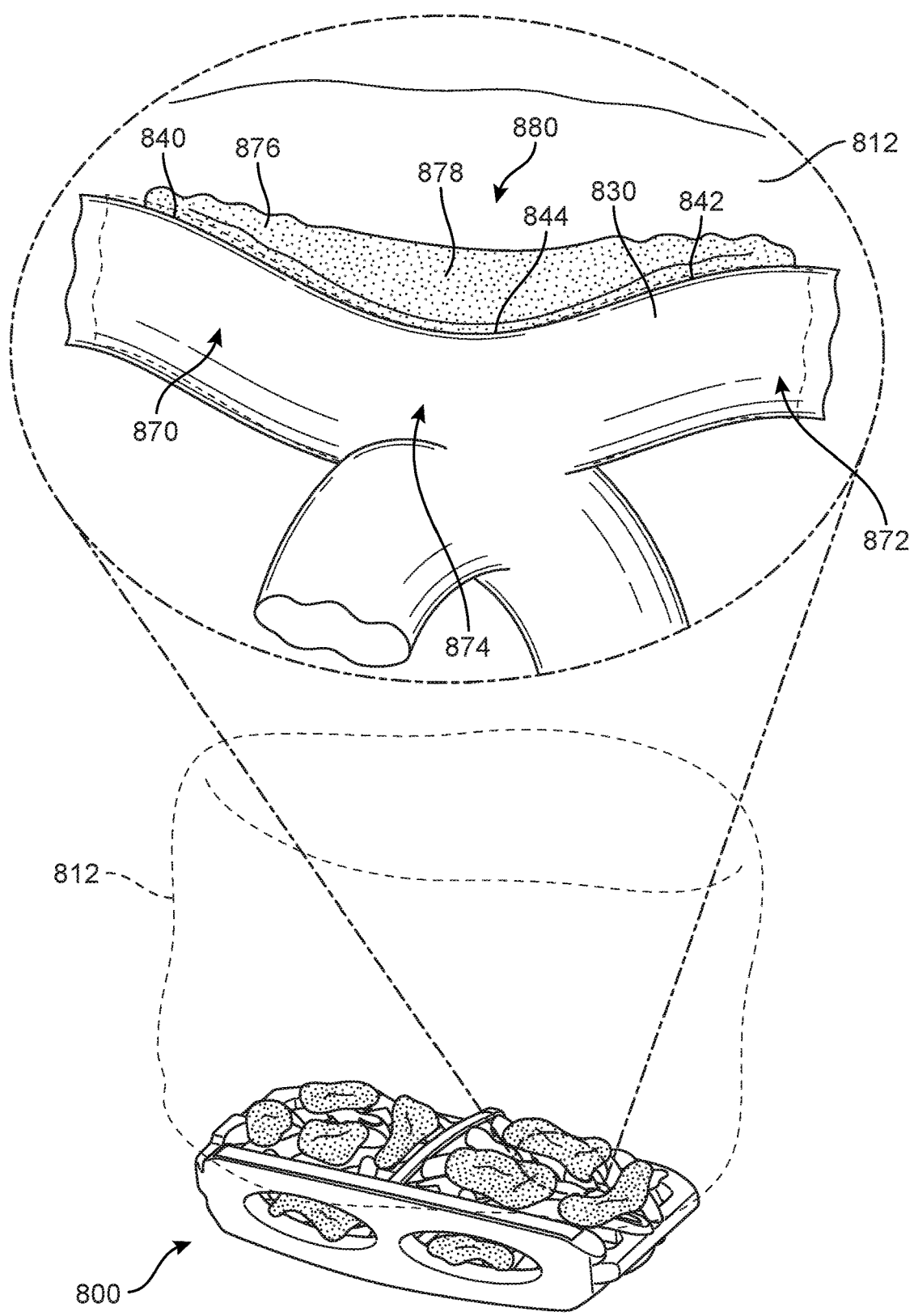
FIG. 24 is a schematic isometric view of the implant of FIG. 23 as an outer member undergoes deformation.
Figure 25:
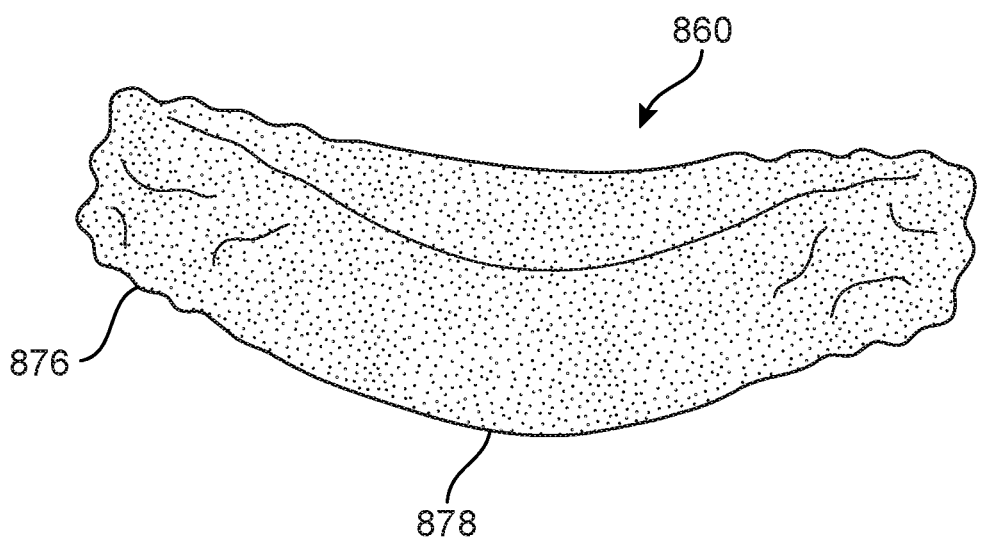
FIG. 25 is a schematic isometric view of the portion of bone growth promoting material of FIG. 23.

FIGS. 23-25 illustrate isometric views intended to depict how a protected fusion zone can help protect new bone growth. In FIG. 23, the enlarged isometric view depicts a BGPM portion 860 that is disposed within protected fusion zone 880. Here, a BGPM portion is any portion of a bone growth promoting material. It may be appreciated that although this embodiment depicts protecting BGPM portion 860, similar principles could apply to any new bone growth disposed in the protected fusion zone 880, including any portions of bone graft or synthetic bone graft as well as any portions of a vertebra growing into protected fusion zone 880. Still further, it may be understood that a protected fusion zone 880 may similarly protect portions of fused material, including fused bone graft and vertebral material.

In FIG. 24, outer member 830 undergoes deformation a load is applied to outer member 830 or adjacent portions of implant 800. Because outer member 830 is supported by support member 832 adjacent proximal surface region 844, the deformation of outer member 830 adjacent to proximal surface region 844 is minimized compared to the deformation of outer member 830 away from proximal surface region 844. More specifically, portion 874 of outer member 830 corresponding to proximal surface region 844 undergoes little deformation compared to portion 870 of outer member 830 corresponding to first distal surface region 840. Likewise, portion 874 undergoes little deformation compared to portion 872 of outer member 830 corresponding to second distal surface region 842. These differences in the degree of deformation may cause greater disturbances to the peripheral segments 876 of BGPM portion 860 that are located adjacent portion 870 and portion 872 of outer member. In contrast, the central segment 878 of BGPM portion 860 that is located adjacent portion 874 of outer member 830 is disturbed significantly less than peripheral segments 876. It may be appreciated that these "disturbances" in the segments of BGPM portion 860 may occur due to microscopic and/or macroscopic motions between adjacent surfaces of outer member 830 and BGPM portion 860.

This difference in the amount of disturbance over different segments of BGPM portion 860 can be seen in FIG. 25. FIG. 25 shows that peripheral segments 876 of BGPM portion 860 are more deformed while central segment 878 is relatively smoother. By minimizing the disturbances of BGPM or other materials in protected fusion zone 880, new bone growth can be protected during intermediate stages of bone growth along implant 800.

In different embodiments, features of the body and/or the structural members could be varied. In some embodiments, the body could lack a central keel portion and/or a base frame portion. In other embodiments, one or more structural members could be arranged in a different pattern from the two examples shown in the embodiment of FIGS. 1-12 and the embodiment of FIGS. 13-15.

The above description details protected fusion zones located on the superior or inferior surfaces of an implant. However, it may be appreciated that an implant can be provided with protected fusion zones in other locations as well. For example, the region beneath a support member, which may have an arch-like shape, can provide a protected fusion zone within an interior of the implant. Such interior protected fusion zones may help protect new bone growth in regions inside the inferior and superior surfaces, which further helps in promoting fusion through the entire thickness of an implant.

Using multiple protected fusion zones throughout an implant may help achieve fusion through the entire implant. In particular, new bone growth grown on the superior and inferior surfaces of an implant may continue to grow into an interior cavity or space of the implant until a continuous fused structure extends from one vertebral body, through the implant to the opposing vertebral body. As new bone growth occurs along the surface of an implant as well as throughout the interior (e.g., along and between the inner support members the and through openings in the frame) the BGPM may be fused into a continuous structure that spans between adjacent vertebrae. Eventually, new bone growth may fuse into a load supporting structure within which implant is embedded. At this point the body and/or structural members of the implant may act to reinforce the newly fused bone structure.

Alternative Embodiment

Figure 26:
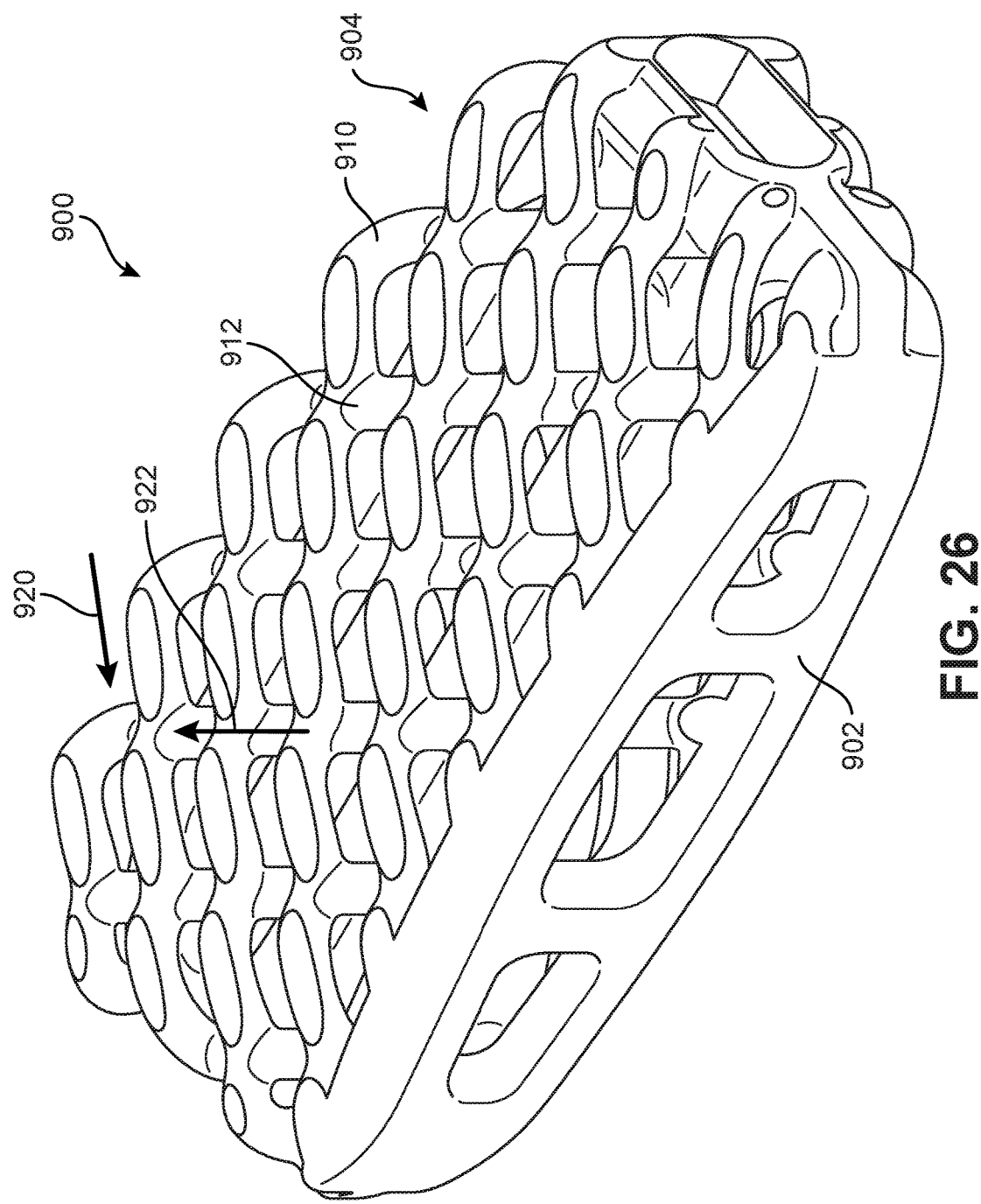
FIG. 26 is a schematic isometric view of another embodiment of an implant.

FIG. 26 is a schematic isometric view of an alternative embodiment of an implant 900. Implant 900 may include similar provisions to other implants discussed herein, including implant 100 (see FIGS. 1-2) and implant 700 (see FIG. 13). In particular, implant 900 includes a body 902 and a plurality of structural members 904. In contrast to earlier embodiments, however, body 902 does not include a central keel portion associated approximately with a median plane of implant 900. Moreover, in the embodiment of FIG. 23, structural members 904 may be arranged in a more regular configuration. Specifically, a plurality of outer members 910 are oriented in parallel with one another along a common direction 920. In addition, plurality of support members 912 are oriented in parallel with one another along a common direction 922, which is perpendicular to direction 920. Thus, plurality of structural members 904 may be seen to form a more regular three-dimensional lattice or cage configuration.

General Dimensions of Implant

The implants for use in the spine have overall dimensions suitable for insertion in the spine, typically between two vertebral bodies. The shape of the implant and dimensions depends on the site into which it is inserted. Exemplary heights for implants such as implant 100, implant 700 and implant 800 include, but are not limited to: 5 mm to 30 mm. Of course other embodiments could have incremental heights of any value in the range between the aforementioned range, most often between 8 mm and 16 mm. Still other embodiments could have a height greater than 16 mm. Still other embodiments could have a height less than 8 mm. Additionally, the horizontal foot-print of the implant could vary. Exemplary foot-print sizes for any embodiments of the implant include, but are not limited to: 15-20 mm in the anterior-posterior direction and 40-60 mm in the lateral-lateral direction. Still other embodiments could be configured with any other footprint sizes.

The dimensions of one or more structural members could vary. In some embodiments, a structural member could have a cross-sectional diameter in a range between 0.2 and 3 mm. For structural members with polygonal cross-sections, the dimensions characterizing the polygon (e.g., first and second diameters for an ellipse) could vary. As an example, a structural member with an elliptic cross-section could have a cross-section with a first diameter in a range between 0.2 mm and 3 mm and a second diameter in range between 0.2 mm and 3 mm. In other embodiments, a structural member could have any other cross-sectional diameter. Moreover, in some cases an outer member and a support member could have similar cross-sectional diameters while in other cases an outer member and a support member could have different cross-sectional diameters.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees. In at least some embodiments, the lordotic angle of the implant is accomplished via the geometry of the central keel portion and the side frame portion (posterior or anterior).

Manufacturing and Materials

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136 and F 3001), or $Ti_6$—$Al_4$—V (ASTM F 2989, F 1108 and ASTM F 1472)) and inert, biocompatible polymers, such as polyether ether ketone (PEEK) (e.g. PEEK-OPTIMA®, Invibio Inc and Zeniva Solvay Inc.). Optionally, the implant contains a radiopaque marker to facilitate visualization during imaging.

In different embodiments, processes for making an implant can vary. In some embodiments, the entire implant may be manufactured and assembled via readditional/CNC machining, injection-molding, casting, insert-molding, co-extrusion, pultrusion, transfer molding, overmolding, compression molding, 3-Dimensional (3-D) printing (including Direct Metal Laser Sintering and Electron Beam Melting), dip-coating, spray-coating, powder-coating, porous-coating, milling from a solid stock material and their combinations. Moreover, the embodiments can make use of any of the features, parts, assemblies, processes and/or methods disclosed in the "Coiled Implants" application.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a body including a base portion and a keel portion;
the keel portion oriented at a nonzero angle to the base portion;
a bone contacting outer member having an elongate geometry, the outer member including a first outer member end and a second outer member end;
a support member having an elongate geometry, the support member including a first support member end and a second support member end;
wherein the first outer member end is attached to the base portion and the second outer member end is attached to the keel portion;
wherein the first support member end is attached to the base portion and wherein the second support member end is attached to the base portion;
wherein the support member is attached to the outer member;
wherein the outer member has a central member curve; and
wherein the central member curve includes a winding segment, and wherein the winding segment of the central member curve winds around a fixed path.

2. The implant according to claim 1, wherein the implant is an intervertebral implant; and
wherein the outer member has a bone contacting outer surface configured to contact a vertebra.

3. The implant according to claim 1, wherein the geometry of the outer member provides a first distal surface region, a proximal surface region and a second distal surface region, wherein the first distal surface region, the proximal surface region and the second distal surface region are all oriented outwardly on a superior side or an inferior side of the implant.

4. The implant according to claim 3, wherein the support member attaches to the outer member at a portion of the outer member including the proximal surface region.

5. The implant according to claim 1, wherein the support member has a curved path that includes an arch-like path.

6. The implant according to claim 1, wherein the outer member has a greater length than the support member.

7. The implant according to claim 1, wherein the implant includes a median plane extending between an anterior side and a posterior side of the implant, the median plane dividing the implant into a first lateral half and a second lateral half; and wherein the keel portion is aligned with the median plane.

8. The implant according to claim 1, wherein the implant includes a transverse plane dividing the implant into a superior half and an inferior half; and wherein the base portion is aligned with the transverse plane.

9. An implant, comprising:
a body, the body defining a transverse plane dividing the implant into a superior half and an inferior half;
a first outer member attached to the body, the first outer member having an elongate geometry;
a second outer member attached to the body, the second outer member having an elongate geometry;
a support member attached to the body, the support member having an elongate geometry;
the support member being attached to the first outer member at a first attachment region and the support member being attached to the second outer member at a second attachment region;

wherein at the first attachment region the support member is disposed closer to the transverse plane than the first outer member is to the transverse plane;

wherein at the second attachment region the support member is disposed closer to the transverse plane than the second outer member is to the transverse plane;

wherein the first outer member has a first central member curve;

wherein the first central member curve includes a first winding segment, and wherein the first winding segment of the first central member curve winds around a first fixed path.

10. The implant according to claim 9, wherein the implant is an intervertebral implant; and wherein the first outer member has a bone contacting outer surface configured to contact a vertebra.

11. The implant according to claim 9, wherein the second outer member has a second central member curve;

wherein the second central member curve includes a second winding segment, and wherein the second winding segment of the second central member curve winds around a second fixed path.

12. The implant according to claim 10, wherein the support member has a curved path that includes an arch-like path.

13. The implant according to claim 9, wherein a length of the support member is less than a length of the first outer member.

14. An implant, comprising:

a body;

an outer member having an elongate geometry, the outer member attached to the body;

a support member having an elongate geometry, the support member attached to the body;

the outer member having an outwardly facing surface portion, wherein the outwardly facing surface portion is a curved surface portion including a first distal surface region, a proximal surface region and a second distal surface region, the proximal surface region being disposed between the first distal surface region and the second distal surface region;

wherein the first distal surface region is configured as a vertebral contacting surface and wherein the second distal surface region is configured as a vertebral contacting surface;

wherein the support member is attached to the outer member at a location proximate the proximal surface region.

15. The implant according to claim 14, wherein the outwardly facing surface portion is disposed on a superior side of the implant.

16. The implant according to claim 14, wherein the outwardly facing surface portion is disposed on an inferior side of the implant.

17. The implant according to claim 14, wherein the outer member has a central member curve;

wherein the central member curve includes a winding segment, and wherein the winding segment of the central member curve winds around a fixed path; and wherein the first distal surface region, the proximal surface region and the second distal surface region are located on a portion of the outer member corresponding to the winding segment.

18. The implant according to claim 17, wherein the outer member is configured to engage a vertebra so as to form a space for protecting bone growth between the vertebra and the proximal surface region.

19. The implant according to claim 18, wherein the implant has an open interior and wherein the implant is configured to receive a bone growth promoting material such that the bone growth promoting agent can extend continuously through the open interior of the implant and into the space for protecting bone growth between the vertebra and the proximal surface region.

20. The implant according to claim 14, wherein the body includes at least one portion with a roughened surface.

21. The implant according to claim 14, wherein the body includes a fastener receiving portion with a threaded opening that is configured to receive an implant tool.

* * * * *